US012064472B2

(12) United States Patent
Perez De Leon et al.

(10) Patent No.: US 12,064,472 B2
(45) Date of Patent: *Aug. 20, 2024

(54) SOUTHERN CATTLE TICK VACCINE PRODUCT

(71) Applicant: The United States of America, as represented by the Secretary of Agriculture, Washington, DC (US)

(72) Inventors: Adalberto A. Perez De Leon, Wake Forest, NC (US); Robert Miller, McAllen, TX (US); Robert E. Briggs, Boone, IA (US); Fred M. Tatum, Nevada, IA (US); Felicito Guerrero, Kerrville, TX (US)

(73) Assignee: The United States of America, as Represented by the Secretary of Agriculture, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/318,909

(22) Filed: May 17, 2023

(65) Prior Publication Data

US 2023/0277638 A1     Sep. 7, 2023

Related U.S. Application Data

(63) Continuation of application No. 17/190,235, filed on Mar. 2, 2021, now Pat. No. 11,690,901.

(60) Provisional application No. 62/984,712, filed on Mar. 3, 2020.

(51) Int. Cl.
| | |
|---|---|
| *A61K 39/02* | (2006.01) |
| *A61K 39/00* | (2006.01) |
| *A61K 39/08* | (2006.01) |
| *A61P 33/14* | (2006.01) |
| *C07K 14/33* | (2006.01) |
| *C07K 14/435* | (2006.01) |

(52) U.S. Cl.
CPC ......... *A61K 39/0003* (2013.01); *A61K 39/08* (2013.01); *A61P 33/14* (2018.01); *C07K 14/33* (2013.01); *C07K 14/43527* (2013.01); *A61K 2039/523* (2013.01); *A61K 2039/53* (2013.01); *A61K 2039/552* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 11,690,901 | B2 | 7/2023 | Leon et al. |
| 2013/0315947 | A1 | 11/2013 | Guerrero, Jr. et al. |
| 2014/0170190 | A1 | 6/2014 | Bey et al. |
| 2014/0212452 | A1 | 7/2014 | Guerrero et al. |
| 2018/0085443 | A1 | 3/2018 | Li et al. |

FOREIGN PATENT DOCUMENTS

| | | |
|---|---|---|
| WO | 2014/159052 | 10/2014 |
| WO | 2004/080375 | 6/2021 |

OTHER PUBLICATIONS

Written Opinion of the International Searching Authority on PCT/US2022/020683 issued Jun. 25, 2021.
International Preliminary Report on Patentability on PCT/US2022/020683 issued Jun. 25, 2021.

*Primary Examiner* — Jennifer E Graser
(74) *Attorney, Agent, or Firm* — John Fado; Maria Restrepo-Hartwig

(57) ABSTRACT

This invention relates to novel fusion peptides and immunogenic compositions containing the fusion peptides useful in the control and prevention of tick infestations. The invention also relates to compositions comprising said fusion peptides, methods of vaccination against tick infestation using said fusion peptides and compositions, and kits for use with such compositions and methods.

11 Claims, 4 Drawing Sheets

Specification includes a Sequence Listing.

SEQUENCE LISTING

```
Sequence total quantity: 21
SEQ ID NO: 1            moltype = DNA  length = 4364
FEATURE                 Location/Qualifiers
source                  1..4364
                        mol_type = genomic DNA
                        organism = Mannheimia haemolytica
SEQUENCE: 1
ttctcttttg ctaaatagtg ttggtaagta gtcccatttt gcacaccaat cgttttcacc    60
ttagcaaaat ctgtatcttt tttcgcaatg aaggcagcag agcttggaaa gtaaggctcg   120
ctaaataata cttgtttctt acgtggttcc gtaatacccca tacctgaaat tgcagcatca   180
aattgttttt gttttaggct ttggattaag ctatcaaaag gttggctatg gaatgtacaa   240
tttgcattca tctctttaca gatagcattt gcaatatcca catcaaaacc gataatttct   300
cccttctctt cggtcatttc aaatggagga tagcttggct ccatcacaaa tttgatatct   360
tgtgcctgcg cagtaaccac acacccgaat aaaagggtca aaagtgtttt tttcataaaa   420
agtccctgtg ttttcattat aaggattacc actttaacgc agttactttc ttaaaaaaag   480
tcttcttttc ataaagtttg ttttatgtca tacaaacaca tcaaattgag atgtagtttc   540
tcaatcctct tgattcctct atctcaaaaa aacaacccaa aagaaaaaag aaaagtatat   600
gttacattaa tattacaatg taattatttt gtttaatttc cctacatttt gtataacttt   660
aaaacactcc tttttctctt ctgattatat aaaagacaaa aaatacaatt taagctacaa   720
aaaacaacaa aaaacaacaa aaaacacgac agtaagatcg agtaatgatt atattatgtt   780
ataatttttg acctaattta gaataattat cgagtgcaaa ttatgaatca atcttatttt   840
aacttactag gaaacattac ttggctatgg atgaactcct ccctccacaa agaatggagc   900
tgtgaactac tagcacgcaa tgtgattcct gcaattgaaa atgaacaata tatgctactt   960
atagataacg gtattccgat cgcttattgt agttgggcag atttaaacct tgagactgag  1020
gtgaaatata ttaaggatat taattcgtta acaccagaag aatggcagtc tggtgacaga  1080
cgctggatta ttgattgggt agcaccattc ggacattctc aattacttta taaaaaaatg  1140
tgtcagaaat accctgatat gatcgtcaga tctatacgct tttatccaaa gcagaaagaa  1200
ttaggcaaaa ttgcctactt taaaggaggt aaattagata aaaaaacagc aaaaaaacgt  1260
tttgatacat atcaagaaga gctggcaaca gcacttaaaa atgaatttaa ttttattaaa  1320
aaatagaagg agacatccct tatgggaact agacttacaa ccctatcaaa tgggctaaaa  1380
aacactttaa cggcaaccaa aagtggctta cataaagccg gtcaatcatt aacccaagcc  1440
ggcagttctt taaaaactgg ggcaaaaaaa attatcctct atattcccca aaattaccaa  1500
tatgatactg aacaaggtaa tggtttacag gatttagtca aagcggccga agagttgggg  1560
attgaggtac aaagagaaga acgcaataat attgcaacag ctcaaaccag tttaggcacg  1620
attcaaaccg ctattggctt aactgagcgt ggcattgtgt tatccgctcc acaaattgat  1680
aaattgctac agaaaactaa agcaggccaa gcattaggtt ctgccgaaag cattgtacaa  1740
aatgcaaata aagccaaaac tgtattatct ggcattcaat ctattttagg ctcagtattg  1800
gctgaatgga atttagatga ggccttacag aataacagca accaacatgc tcttgctaaa  1860
gctggcttgg agctaacaaa ttcattaatt gaaaatattg ctaattcagt aaaaacactt  1920
gacgaatttg gtgagcaaat tagtcaattt ggttcaaaac tacaaaatat caaaggctta  1980
gggacttlag gagacaaact caaaaatatc ggtggacttg ataaagctgg ccttggttta  2040
gatgttatct cagggctatt atcgggcgca acagctgcac ttgtacttgc agataaaaat  2100
```

```
gcttcaacag ctaaaaaagt gggtgcgggt tttgaattgg caaaccaagt tgttggtaat  2160
attaccaaag ccgtttcttc ttacattta gcccaacgtg ttgcagcagg tttatcttca  2220
actgggcctg tggctgcttt aattgcttct actgtttctc ttgcgattag cccattagca  2280
tttgccggta ttgccgataa atttaatcat gcaaaaagtt tagagagtta tgccgaacgc  2340
tttaaaaaat taggctatga cggagataat ttattagcag aatatcagcg gggaacaggg  2400
actattgatg catcggttac tgcaattaat accgcattgg ccgctattgc tggtggtgtg  2460
tctgctgctg cagccggctc ggttattgct tcaccgattg ccttattagt atctgggatt  2520
accggtgtaa tttctacgat tctgcaatat tctaaacaag caatgtttga gcacgttgca  2580
aataaaattc ataacaaaat tgtagaatgg gaaaaaaata atcacggtaa gaactacttt  2640
gaaaatggtt acgatgcccg ttatcttgcg aatttacaag ataatatgaa attcttactg  2700
aacttaaaca aagagttaca ggcagaacgt gtcatcgcta ttactcagca gcaatgggat  2760
aacaacattg tgatttagc tggtattagc cgtttaggtg aaaaagtcct tagtggtaaa  2820
gcctatgtgg atgcgtttga agaaggcaaa cacattaaag ccgataaatt agtacagttg  2880
gattcggcaa acggtattat tgatgtgagt aattcgggta aagcgaaaac tcagcatatc  2940
ttattcagaa cgccattatt gacgccggga acagagcatc gtgaacgcgt acaaacaggt  3000
aaatatgaat atattaccaa gctcaatatt aaccgtgtag atagctggaa attacagat  3060
ggtgcagcaa gttctaccttt tgatttaact aacgttgttc agcgtattgg tattgaatta  3120
gacaatgctg gaaatgtaac taaaaccaaa gaaacaaaaa ttattgccaa acttggtaa  3180
ggtgatgaca acgtatttgt tggttctggt acgacggaaa ttgatggcgg tgaaggttac  3240
gaccgagttc actatagccg tggaaactat ggtgctttaa ctattgatgc aaccaaagag  3300
accgagcaag gtagttatac cgtaaatcgt ttcgtagaaa ccggtaaagc actacacgaa  3360
gtgacttcaa cccataccgc attagtgggc aaccgtgaag aaaaaataga atatcgtcat  3420
agcaataacc agcaccatgc cggttattac accaaagata ccttgaaagc tgttgaagaa  3480
attatcggta catcacataa cgatatcttt aaaggtagta agttcaatga tgcctttaac  3540
ggtggtgatg gtgtcgatac tattgacggt aacgacggca atgaccgctt atttggtggt  3600
aaaggcgatg atattctcga tggtggaaat ggtgatgatt ttatcgatgg cggtaaaggc  3660
aacgacctat tacacggtgg caagggcgat gatattttcg ttcaccgtaa aggcgatggt  3720
aatgatatta ttaccgattc tgacggcaat gataaattat cattctctga ttcgaactta  3780
aaagatttaa catttgaaaa agttaaacat aatcttgtca tcacgaatag caaaaaagag  3840
aaagtgacca ttcaaaactg gttccgagag gctgattttg ctaaagaagt gcctaattat  3900
aaagcaacta aagatgagaa atctgaagaa atcatcggtc aaaatggcga gcggatcacc  3960
tcaaagcaag ttgatgatct tatcgcaaaa ggtaacggca aaattccca agatgagcta  4020
tcaaagttg ttgataacta tgaattgctc aaacatagca aaaatgtgac aaacagctta  4080
gataagttaa tctcatctgt aagtgcattt acctcgtcta atgattcgga tgattcgta  4140
gtggctccaa cttcaatgtt ggatcaaagt ttatcttctc ttcaatttgc tagagcagct  4200
taattttaa tgattggcaa ctctatattg ttttcacacat tatagagttg ccgttttatt  4260
ttataaaagg agacaatatg gaagctaacc atcaaaggaa tgatcttggt ttagttgccc  4320
tcactatgtt ggcacaatac cataatattt cgcttaatcc ggaa              4364

SEQ ID NO: 2            moltype = DNA  length = 839
FEATURE                 Location/Qualifiers
source                  1..839
                        mol_type = other DNA
                        organism = synthetic construct
SEQUENCE: 2
ggatccttta acggtggtga tggtgtcgat actattgacg gtaacgacgg caatgaccgc   60
ttatttggtg gtaaaggcga tgatattctc gatggtgatga atggtgatt tttatcgat  120
ggcggtaaag gcaacgacct attacacggt ggcaagggcg atgatatttt cgttcaccgt  180
aaaggcgatg gtaatgatat tattaccgat tctgacggca atgataaatt atcattctct  240
gattcgaact taaaagattt aacatttgaa aaagttaaac ataatcttgt catcacgaat  300
agcaaaaaag agaaagtgac cattcaaaac tggttccgag aggctgattt tgctaaagaa  360
gtgcctaatt ataaagcaac taaagatgag aaaatcgaag aaatcatcgg tcaaaatggc  420
gagcggatca cctcaaagca agttgatgat cttatcgcaa aaggtaacgg caaaattacc  480
caagatgagc tatcaaaagt tgttgataac tatgaattgc tcaaacatag caaaaatgtg  540
acaaacagct tagataagtt aatctcatct gtaagtgcat ttacctcgtc taatgattcg  600
agaaatgtat tagtggctcc aacttcaatg ttggatcaaa gtttatcttc tcttcaattt  660
gctagagcag cttaattttt aatgattggc aactctatat gtttcacac attatagagt  720
tgccgtttta ttttataaaa ggagacaata tggaagctaa ccatcaaagg aatgatcttg  780
gtttagttgc ccctcactatg ttggcacaat accataatat ttcgcttaat ccggaattc  839

SEQ ID NO: 3            moltype = DNA  length = 24
FEATURE                 Location/Qualifiers
source                  1..24
                        mol_type = other DNA
                        organism = synthetic construct
SEQUENCE: 3
aaaggatcct ttaacggtgg tgat                                           24

SEQ ID NO: 4            moltype = DNA  length = 37
FEATURE                 Location/Qualifiers
source                  1..37
                        mol_type = other DNA
                        organism = synthetic construct
SEQUENCE: 4
aaagaattcc ggattaagcg aaatattatg gtattgt                             37

SEQ ID NO: 5            moltype = DNA  length = 1076
FEATURE                 Location/Qualifiers
source                  1..1076
```

```
                              mol_type = other DNA
                              organism = synthetic construct
SEQUENCE: 5
ggatccgaat tctcttttgc taaatagtgt tggtaagtag tcccattttg cacaccaatc    60
gttttcacct tagcaaaatc tgtatctttt ttcgcaatga aggcagcaga gcttggaaag   120
taaggctcgc taaataatac ttgtttctta cgtggttccg taatacccat acctgaaatt   180
gcagcatcaa attgtttttg ttttaggctt tggattaagc tatcaaaagg ttggctatgg   240
aatgtacaat ttgcattcat ctctttacag atagcatttg caatatccac atcaaaaccg   300
ataatttctc ccttctcttc ggtcatttca aatggaggat agcttggctc catcacaaat   360
ttgatatctt gtgcctgcgc agtaaccaca cacccgaata aaagggtcaa aagtgttttt   420
ttcataaaaa gtccctgtgt tttcattata aggattacca ctttaacgca gttactttct   480
taaaaaaagt cttcttttca taagtttgt tttatgtcat acaaacacat caaattgaga   540
tgtagtttct caatcctctt gattcctcta tctcaaaaaa acaacccaaa agaaaaaaga   600
aaagtatatg ttacattaat attacaatgt aattattttg tttaatttcc ctacattttg   660
tataacttta aaacactcct ttttctcttc tgattatata aaagacaaaa aatacaattt   720
aagctacaaa aaacaacaaa aaacaacaaa aaacacgaca ataagatcga gtaatgatta   780
tattatgtta taattttga cctaatttag aataattata ggagacatcc cttatgcaat   840
tggtaattac aaatagcaaa aagaaaaag taacaattca aaattggttt cgtgaagcag   900
atttcgctaa agaagttcca aattataaag caacgaagga tgaaaaaatt gaagaaatta   960
ttggacaaaa tggagaacgt attacaagta acaagtaga tgacttaatc gcaaaaggta  1020
acggaaaaat tactcaggat gaattatcga aggtggtaga taactatgaa ggatcc      1076

SEQ ID NO: 6              moltype = DNA  length = 810
FEATURE                   Location/Qualifiers
source                    1..810
                          mol_type = other DNA
                          organism = Mannheimia haemolytica
SEQUENCE: 6
ttctcttttg ctaaatagtg ttggtaagta gtcccatttt gcacaccaat cgttttcacc    60
ttagcaaaat ctgtatcttt tttcgcaatg aaggcagcag agcttggaaa gtaaggctcg   120
ctaaataata cttgtttctt acgtggttcc gtaatacccca tacctgaaat tgcagcatca   180
aattgttttt gttttaggct ttggattaag ctatcaaaag gttggctatg gaatgtacaa   240
tttgcattca tctctttaca gatagcattt gcaatatcca catcaaaacc gataatttct   300
ccttctctt cggtcatttc aaatggagga tagcttggct ccatcacaaa tttgatatct   360
tgtgcctgcg cagtaaccac acacccgaat aaaagggtca aaagtgtttt ttcataaaa   420
agtccctgtg ttttcattat aaggattacc actttaacgc agttactttc ttaaaaaaag   480
tcttcttttc ataagtttg ttttatgtca tacaaacaca tcaaattgag atgtagtttc   540
tcaatcctct tgattcctct atctcaaaaa aacaacccaa aagaaaaag aaaagtatat   600
gttacattaa tattacaatg taattatttt gtttaatttc cctacatttt gtataacttt   660
aaaacactcc ttttctctt ctgattatat aaaagacaaa aatacaatt taagctacaa   720
aaaacaacaa aaaacaacaa aaaacacgac aataagatcg agtaatgatt atattatgtt   780
ataattttg acctaattta gaataattat                                     810

SEQ ID NO: 7              moltype = DNA  length = 15
FEATURE                   Location/Qualifiers
source                    1..15
                          mol_type = other DNA
                          organism = Mannheimia haemolytica
SEQUENCE: 7
aaggagacat ccctt                                                     15

SEQ ID NO: 8              moltype = DNA  length = 240
FEATURE                   Location/Qualifiers
source                    1..240
                          mol_type = other DNA
                          organism = synthetic construct
SEQUENCE: 8
caattggtaa ttacaaatag caaaaagaa aaagtaacaa ttcaaaattg gtttcgtgaa    60
gcagatttcg ctaaagaagt tccaaattat aaagcaacga aggatgaaaa aattgaagaa   120
attattggac aaaatggaga acgtattaca agtaaacaag tagatgactt aatcgcaaaa   180
ggtaacggaa aaattactca ggatgaatta tcgaaggtgg tagataacta tgaaggatcc   240

SEQ ID NO: 9              moltype = AA   length = 80
FEATURE                   Location/Qualifiers
source                    1..80
                          mol_type = protein
                          organism = synthetic construct
SEQUENCE: 9
QLVITNSKKE KVTIQNWFRE ADFAKEVPNY KATKDEKIEE IIGQNGERIT SKQVDDLIAK    60
GNGKITQDEL SKVVDNYEGS                                                80

SEQ ID NO: 10             moltype = DNA  length = 832
FEATURE                   Location/Qualifiers
source                    1..832
                          mol_type = other DNA
                          organism = Mannheimia haemolytica
SEQUENCE: 10
cctttaacgg tggtgatggt gtcgatacta ttgacggtaa cgacggcaat gaccgcttat    60
ttggtggtaa aggcgatgat attctcgatg gtggaaatgg tgatgatttt atcgatggcg   120
```

-continued

```
gtaaaggcaa cgacctatta cacggtggca agggcgatga tattttcgtt caccgtaaag    180
gcgatggtaa tgatattatt accgattctg acggcaatga taaattatca ttctctgatt    240
cgaacttaaa agatttaaca tttgaaaaag ttaaacataa tcttgtcatc acgaatagca    300
aaaaagagaa agtgaccatt caaaactggt tccgagaggc tgattttgct aaagaagtgc    360
ctaattataa agcaactaaa gatgagaaaa tcgaagaaat catcggtcaa aatggcgagc    420
ggatcacctc aaagcaagtt gatgatctta tcgcaaaagg taacggcaaa attacccaag    480
atgagctatc aaagttgtt gataactatg aattgctcaa acatagcaaa aatgtgacaa    540
acagcttaga taagttaatc tcatctgtaa gtgcatttac ctcgtctaat gattcgagaa    600
atgttattagt ggctccaact tcaatgttgg atcaaagttt atcttctctt caatttgcta    660
gagcagctta atttttaatg attggcaact ctatattgtt tcacacatta tagagttgcc    720
gttttatttt ataaaaggag acaatatgga agctaaccat caaaggaatg atcttggttt    780
agttgccctc actatgttgg cacaatacca taatatttcg cttaatccgg aa           832

SEQ ID NO: 11         moltype = AA   length = 282
FEATURE               Location/Qualifiers
source                1..282
                      mol_type = protein
                      organism = Mannheimia haemolytica
SEQUENCE: 11
ELVITNSKKE KVTIQNWFRE ADFAKEVPNY KATKDEKIEE IIGQNGERIT SKQVDDLIAK     60
GNGKITQDEL SKVVDNYEGS FNGGDGVDTI DGNDGNDRLF GGKGDDILDG GNGDDFIDGG    120
KGNDLLHGGK GDDIFVHRKG DVKDLTFEKV KHNLVITNSK KEKVTIQNWF READFAKEVP    180
NYKATKDEKI EEIIGQNGER ITSKQVDDLI AKGNGKITQD ELSKVVDNYE LLKHSKNVTN    240
SLDKLISSVS AFTSSNDSRN VLVAPTSMLD QSLSSLQFAR AA                       282

SEQ ID NO: 12         moltype = DNA   length = 1903
FEATURE               Location/Qualifiers
source                1..1903
                      mol_type = other DNA
                      organism = synthetic construct
SEQUENCE: 12
gaattctctt ttgctaaata gtgttggtaa gtagtcccat tttgcacacc aatcgttttc     60
accttagcaa aatctgtatc ttttttcgca atgaaggcag cagagcttgg aaagtaaggc    120
tcgctaaata atacttgttt cttacgtggt tccgtaatca ccatacctga aattgcagca    180
tcaaattgtt tttgttttag gctttggatt aagctatcaa aaggttggct atggaatgta    240
caatttgcat tcatctcttt acagatagca tttgcaatat ccacatcaaa accgataatt    300
tctcccttct cttcggtcat ttcaaatgga ggatagcttg gctccatcac aaatttgata    360
tcttgtgcct gcgcagtaac cacacacccg aataaagggg tcaaagtgt ttttttcata    420
aaaagtccct gtgttttcat tataaggatt accacttta cgcagttact ttcttaaaaa    480
aagtcttctt ttcataaagt ttgttttatg tcatacaaac acatcaaatt gagatgtagt    540
ttctcaatcc tcttgattcc tctatctcaa aaaacaacc caaagaaaa agaaaagta    600
tatgttacat taatattaca atgtaattat tttgtttaat ttccctacat tttgtataac    660
tttaaaacac tccttttct cttctgatta tataaaagc aaaaaatca atttaagcta    720
caaaaaacaa caaaaaacaa caaaaaacac gacaataaga tcgagtaatg attatattat    780
gttataattt tgacctaat ttagaataat tataggagac atcccttatg caattggtaa    840
ttacaaatag caaaaaagaa aaagtaacaa ttcaaaattg gtttcgtgaa gcagatttcg    900
ctaaagaagt tccaaattat aaagcaacga aggatgaaaa attgaagaa attattggac    960
aaaatggaga acgtattaca agtaaacaag tagatgactt aatcgcaaaa ggtaacggaa   1020
aaattactca ggatgaatta tcgaaggtgg tagataacta tgaaggatcc tttaacggtg   1080
gtgatggtgt cgatactatt gacggtaacg acggcaatga ccgcttattt ggtggtaag    1140
gcgatgatat tctcgatggt ggaaatggtg atgattttat cgatggcggt aaaggcaacg   1200
acctattaca cggtggcaag ggcgatgata ttttcgttca ccgtaaaggc gatggtaatg   1260
atattattac cgattctgac ggcaatgata aattatcatt ctctgattcg aacttaaaag   1320
atttaacatt tgaaaaagtt aaacataatc ttgtcatcac gaatagcaaa aaagagaaag   1380
tgaccattca aaactggttc cgagaggctg attttgctaa agaagtgcct aattataaag   1440
caactaaaga tgagaaaatc gaagaaatca tcggtcaaaa tggcgagcgg atcacctcaa   1500
agcaagttga tgatcttatc gcaaaaggta acggcaaaat tacccaagat gagctatcaa   1560
agttgttga taactatgaa ttgctcaaac atagcaaaaa tgtgacaaac agcttagata   1620
agttaatctc atctgtaagt gcatttacct cgtctaatga ttcgagaaat gttagtagt    1680
ctccaacttc aatgttggat caaagtttat cttctcttca atttgctaga gcagcttaat   1740
ttttaatgat tggcaactct atattgtttc acacattata gagttgccgt tttatttat    1800
aaaaggagac aatatggaag ctaaccatca aaggaatgat cttggtttag ttgccctcac   1860
tatgttggca caataccata atatttcgct taatccggaa ttc                     1903

SEQ ID NO: 13         moltype = AA   length = 303
FEATURE               Location/Qualifiers
source                1..303
                      mol_type = protein
                      organism = synthetic construct
SEQUENCE: 13
MQLVITNSKK EKVTIQNWFR EADFAKEVPN YKATKDEKIE EIIGQNGERI TSKQVDDLIA     60
KGNGKITQDE LSKVVDNYEG SFNGGDGVDT IDGNDGNDRL FGGKGDDILD GGNGDDFIDG    120
GKGNDLLHGG KGDDIFVHRK GDGNDIITDS DGNDKLSFSD SNLKDLTFEK VKHNLVITNS    180
KKEKVTIQNW FREADFAKEV PNYKATKDEK IEEIIGQNGE RITSKQVDDL IAKGNGKITQ    240
DELSKVVDNY ELLKHSKNVT NSLDKLISSV SAFTSSNDSR NVLVAPTSML DQSLSSLQFA    300
RAA                                                                  303

SEQ ID NO: 14         moltype = AA   length = 16
FEATURE               Location/Qualifiers
```

```
source                  1..16
                        mol_type = protein
                        organism = synthetic construct
SEQUENCE: 14
FQYIKANSKF IGITEQ                                                16

SEQ ID NO: 15           moltype = DNA  length = 48
FEATURE                 Location/Qualifiers
source                  1..48
                        mol_type = other DNA
                        organism = synthetic construct
SEQUENCE: 15
ttccaataca ttaaagcaaa ttcaaaattc attggcatta cggaacaa             48

SEQ ID NO: 16           moltype = AA   length = 54
FEATURE                 Location/Qualifiers
source                  1..54
                        mol_type = protein
                        organism = Rhipicephalus microplus
SEQUENCE: 16
LALVFATYKD AIEHFDQGIR QVTGEKATAG IFATYPRPHV STLTCFIDQV IATE       54

SEQ ID NO: 17           moltype = DNA  length = 162
FEATURE                 Location/Qualifiers
source                  1..162
                        mol_type = other DNA
                        organism = synthetic construct
SEQUENCE: 17
ttggctttag tttttgcaac ctacaaagat gctattgaac attttgatca ggtattcgt  60
caagttacag gtgaaaaagc aaccgcaggt attttttgcaa cctatcctcg tccacatgta 120
agtactttaa cttgttttat tgatcaagta attgccactg aa                   162

SEQ ID NO: 18           moltype = DNA  length = 1266
FEATURE                 Location/Qualifiers
source                  1..1266
                        mol_type = other DNA
                        organism = synthetic construct
SEQUENCE: 18
ttccaataca ttaaagcaaa ttcaaaattc attggcatta cggaacaatt ccaatacatt  60
aaagcaaatt caaaattcat tggcattacg aacaattgg ctttagtttt tgcaacctac 120
aaagatgcta ttgaacattt tgatcagggt attcgtcaag ttacaggtga aaaagcaacc 180
gcaggtattt ttgcaacctaa tcctcgtcca catgtaagta ctttaacttg ttttattgat 240
caagtaattg ccactgaatt ggctttagtt tttgcaacct acaaagatgc tattgaacat 300
tttgatcagg gtattcgtca agttacaggt gaaaaagcaa ccgcaggtat ttttgcaacc 360
tatcctcgtc cacatgtaag tactttaact tgttttattg atcaagtaat tgccactgaa 420
ttggtaatta caaatagcaa aaagaaaaa gtaacaattc aaaattggtt tcgtgaagca 480
gatttcgcta aagaagttcc aaattataaa gcaacgaagg atgaaaaatt gaagaaatt 540
attggacaaa atggagaacg tattacaagt aaacaagtag atgacttaat cgcaaaaggt 600
aacgaaaaa ttactcagga tgaattatcg aaggtggtag ataactatga aggatccttt 660
aacggtggta atggtgtcga tactattgac ggtaacgacg gcaatgaccg cttatttggt 720
ggtaaaggcg atgatattct cgatggtgga aatggtagta attttatcg tggcggtaaa 780
ggcaacgacc tattacacgg tggcaagggc gatgataatt tcgttcaccg taaaggcgat 840
gtaaagatt taacatttga aaaagttaaa cataatcttg tcatcacgaa tagcaaaaaa 900
gagaaagtga ccattcaaaa ctggttccga gaggctgatt ttgctaaaga agtgcctaat 960
tataaagcaa ctaaagatga gaaaatcgaa gaaatcgaa gtcaaaatgg cgagcggatc 1020
acctcaaagc aagttgatga tcttatcgca aaaggtaacg gcaaaattac ccaagatgag 1080
ctatcaaaag ttgttgataa ctatgaattg tcaaacata gcaaaatgt gacaaacagc 1140
ttagataagt taatctcatc tgtaagtgca tttacctcgt ctaatgattc gagaaatgta 1200
ttagtggctc caacttcaat gttggatcaa agtttatctt ctcttcaatt tgctagagca 1260
gcttaa                                                          1266

SEQ ID NO: 19           moltype = AA   length = 422
FEATURE                 Location/Qualifiers
source                  1..422
                        mol_type = protein
                        organism = synthetic construct
SEQUENCE: 19
QFQYIKANSK FIGITEQFQY IKANSKFIGI TEQLALVFAT YKDAIEHFDQ GIRQVTGEKA  60
TAGIFATYPR PHVSTLTCFI DQVIATELAL VFATYKDAIE HFDQGIRQVT GEKATAGIFA 120
TYPRPHVSTL TCFIDQVIAT ELVITNSKKE KVTIQNWFRE ADFAKEVPNY KATKDEKIEE 180
IIGQNGERIT SKQVDDLIAK GNGKITQDEL SKVVDNYEGS FNGGDGVDTI DGNDGNDRLF 240
GGKGDDILDG GNGDDFIDGG KGNDLLHGGK GDDIFVHRKG DVKDLTFEKV KHNLVITNSK 300
KEKVTIQNWF READFAKEVP NYKATKDEKI EEIIGQNGER ITSKQVDDLI AKGNGKITQD 360
ELSKVVDNYE LLKHSKNVTN SLDKLISSVS AFTSSNDSRN VLVAPTSMLD QSLSSLQFAR 420
AA                                                              422

SEQ ID NO: 20           moltype = AA   length = 56
FEATURE                 Location/Qualifiers
source                  1..56
```

|   |   |   |
|---|---|---|
| | mol_type = protein<br>organism = synthetic construct | |
| SEQUENCE: 20 | | |
| SGSGALVFAT YKDAIEHFDQ GIRQVTGEKA TAGIFATYPR PHVSTLTCFI DQVIAT | | 56 |
| | | |
| SEQ ID NO: 21<br>FEATURE<br>source | moltype = AA  length = 36<br>Location/Qualifiers<br>1..36<br>mol_type = protein<br>organism = synthetic construct | |
| SEQUENCE: 21 | | |
| SGSGFREADF AKEVPNYKAT KDEKIEEIIG QNGERI | | 36 |

SOUTHERN CATTLE TICK VACCINE PRODUCT

CROSS-REFERENCE TO RELATED APPLICATIONS

This application is a continuation of U.S. application Ser. No. 17/190,235, filed Mar. 2, 2021, now allowed, which claims priority benefit from U.S. Provisional Application No. 62/984,712, filed Mar. 3, 2020. The contents of these patent applications are hereby expressly incorporated by reference in their entirety.

FIELD OF THE INVENTION

This invention relates to novel fusion peptides and immunogenic compositions containing the fusion peptides useful in the control and prevention of tick infestations. The invention also relates to compositions comprising said fusion peptides, methods of vaccination against tick infestation using said fusion peptides and compositions, and kits comprising such fusion peptides, and compositions.

SEQUENCE LISTING

The instant application contains a Sequence Listing XML required by 37 C.F.R. § 1.831(a) which has been submitted in XML file format via the USPTO patent electronic filing system, and is hereby incorporated by reference in its entirety. The XML file was created on 05/16/2023, is named Sequence_Listing-005423.xml, and has 31.1 KB.

BACKGROUND OF THE INVENTION

The southern cattle fever tick (SCFT), *Rhipicephalus (Boophilus) microplus* (*R. microplus*) is considered the most economically important external parasite of livestock worldwide. In addition to direct deleterious effects on animal health and production, the SCFT transmits pathogens that cause bovine babesiosis and anaplasmosis. Bovine babesiosis causes the highest economic losses globally among diseases of livestock transmitted by ticks, mosquitoes, or other external parasites and disease vectors with jointed legs, or arthropods. Even though it was eradicated from the USA in 1943, the SCFT remains a threat to the livestock industry in the USA because it is established in Mexico. All cattle presented for importation into the USA at the Texas-Mexico border are treated with acaricides to prevent reintroduction. However, there is a risk of the reestablishment of this tick in the United States due to the presence of acaricide-resistant cattle tick populations.

Commercial vaccines to protect cattle from diseases caused by organisms transmitted by the cattle tick *R. microplus* currently exist. For example, Combavac 3 in 1 live tick fever vaccine is produced by the Queensland Department of Agriculture Fisheries and Forestry in Wacol, Queensland, Australia; Bm86 immunomodulator is produced by Zoetis, Parsippany-Troy Hills, New Jersey, USA. Combavac 3 in 1 is not registered in the USA and only protects against the diseases (babesia and anaplasmosis) ticks carry. Bm86 immunomodulator kills ticks. However, while it protects very well against *R. annulatus*, essentially 100% control, it is only 30-40% effective against *R. microplus* found in the Americas. Bm86 immunomodulator requires an initial injection and a booster injection after 4 weeks. Additionally, booster injections are required every 6 months to keep antibody levels high in host cattle.

Use of bacterial vectors as vehicles to deliver recombinant antigens emerged in the late 1990s. Bacteria-based antigen delivery vectors exhibit multiple advantages, such as the possibility to control its intrinsic infectious power, its non-integrative properties, ability to regulate the amount and in vivo localization of the antigen, a potential for multiple vaccine delivery routes, potent stimulation of the innate and adaptive immune systems, and relatively low manufacturing costs. Bacterial vectors most frequently used as vaccine vectors are *Listeria* and *Salmonella*.

Aquaporin (AQP) is a transmembrane protein family that forms pores to transport water and small solutes across cellular membranes (Borgnia M, et al., 1999, "*Cellular and molecular biology of the aquaporin water channels,*" *Annu. Rev. Biochem.* 68:425-458). Members of the AQP family have been identified throughout the plant and animal kingdoms (Gonen T and Walz T, 2006, "*The structure of aquaporins,*" *Q. Rev. Biophys.* 39:361-396). AQP structures are conserved among species, having six transmembrane domains that are connected by two intracellular loops and three extracellular loops. Two asparagine-proline-alanine (NPA) motifs are considered AQP signature motifs and are located at the protein portions that interact to form a pore. At least 13 AQP members have been identified so far and classed into two subsets: those permeated by water and those permeated by water plus other small molecules, such as glycerol and urea.

U.S. Pat. No. 8,722,063 discloses nucleotide and amino acid sequences of *R. microplus* aquaporin 1 (RmAQP1) and TC5777 gut membrane protein. Polynucleotide fragments encoding at least 197 RmAQP1 amino acids, or at least 219 TC5777 amino acids were tested as antigens to reduce tick viability and reproduction. Compositions comprising at least amino acids 3 to 198 of aquaporin, at least amino acids 1 to 219 of TC5777 gut membrane protein, or a chimera comprising at least amino acids 3 to 198 of aquaporin and at least amino acids 1 to 219 of TC5777 gut membrane protein proved effective in eliciting in livestock a protective immune response to control and prevent infestations by *R. microplus*. While the recombinant form of RmAQP1 proved to be an effective immunogen, issues were encountered when attempting to produce useful quantities of the antigen in yeast.

At the amino acid level, the *R. microplus* aquaporin 2 (RmAQP2) is 42% identical to RmAQP1, but 85% identical to a *Dermacentor variabilis* aquaporin. RmAQP2 is expressed in salivary glands. U.S. Pat. No. 10,052,369 discloses the use of an RmAQP2 polypeptide of at least 290 amino acids in immunogenic compositions to stimulate an immune response to *R. microplus* in ungulates.

U.S. Pat. No. 10,363,292 discloses the use of *R. microplus* Rm86Texas as an immunogen to reduce tick infestation in non-bovine animals. The polynucleotide encoding Rm86Texas was expressed as a recombinant protein in the yeast *Pichia pastoris*. A formulation of protein antigen plus adjuvant was used as vaccine.

U.S. Pat. No. 9,370,561, issued Jun. 21, 2016, discloses the modification of the *M. haemolytica* strain A1 lktCA gene cluster by an in-frame deletion of the nucleotides encoding amino acid 4 of lktC to the nucleotides encoding amino acid 707 of lktA, and replacement of the lktC ribosome binding site (rbs) with an *E. coli* consensus rbs. Electrocompetent *M. haemolytica* cells were transformed with the modified lktCA gene cluster resulting in attenuated bacterium. U.S. Pat. No. 9,370,561 claims a vaccine comprising live, attenuated *M. haemolytica* A1 and A6 strains containing nucleic acid deletions in their respective lktA genes, that provide protective immune response against disease caused by *M. haemolytica* strains A1 and A6.

U.S. Pat. No. 6,331,303, issued Dec. 18, 2001, discloses *P. haemolytica* bacterium which expresses no biologically active leukotoxin, expresses a leukotoxin molecule lacking amino acids 34 to 378, and contains no foreign DNA. In 1999, *P. haemolytica* was renamed as *Mannheimia haemolytica*.

Thus, a vaccine that provides consistent and efficacious protection against *R. microplus*, and that may be produced in useful quantities is desperately needed.

SUMMARY OF THE INVENTION

Provided herein are polynucleotides encoding at least one copy of a tetanus toxin P2 epitope (P2 epitope) and at least one copy of a tick aquaporin 1 (AQP1) protein fragment. Disclosed herein is also a modified *M. haemolytica* lktCA gene cluster cassette comprising a polynucleotide fragment encoding an additional leukotoxin neutralizing epitope, and encoding at least one copy of a P2 epitope and at least one copy of the AQP1 protein fragment.

In an embodiment, the invention relates to a polynucleotide encoding at least one copy of a tick aquaporin 1 protein (AQP1) fragment and a at least one copy of a tetanus toxin P2 epitope (P2 epitope). In some embodiments of the invention, the tick AQP1 fragment is a *R. microplus* AQP1 (RmAQP1) fragment in the polynucleotide encoding at least one copy of a tick AQP1 fragment and a at least one copy of a P2 epitope. In some embodiments of the invention, the polynucleotide encodes two copies of the AQP1 fragment. In some embodiments of the invention, the polynucleotide encodes one copy of a P2 epitope. In some embodiments of the invention, the polynucleotide encodes two copies of a P2 epitope.

In an embodiment, the invention relates to a modified *M. haemolytica* lktCA gene cluster cassette comprising an insertion of a polynucleotide encoding an additional leukotoxin neutralizing epitope and at least one copy of a tick AQP1 fragment, wherein the polynucleotide is inserted downstream of the native leukotoxin A start codon.

In some embodiments of the invention, the modified *M. haemolytica* lktCA gene cluster cassette comprises, in a 5' to 3' orientation, a leukotoxin promotor polynucleotide; a leukotoxin A ribosome binding site and start codon polynucleotide; a polynucleotide encoding an added leukotoxin neutralizing epitope; a polynucleotide encoding at least one copy of a tick AQP1 fragment; and a polynucleotide encoding at least native leukotoxin A amino acids 732 to 953. In some embodiments of the invention, the modified *M. haemolytica* lktCA gene cluster cassette further comprises a polynucleotide encoding at least one copy of a tetanus toxin P2 epitope. In some embodiments of the invention, the modified *M. haemolytica* lktCA gene cluster cassette comprises a polynucleotide encoding two copies of a tick AQP1 fragment. In some embodiments of the invention, the modified *M. haemolytica* lktCA gene cluster cassette comprises a polynucleotide encoding two copies of the P2 epitope. In some embodiments of the invention, the tick AQP1 fragment in the modified *M. haemolytica* lktCA gene cluster cassette is a *R. microplus* AQP1 (RmAQP1) fragment.

In an embodiment, the invention relates to a modified *M. haemolytica* lktCA gene cluster cassette wherein the leukotoxin promotor has the nucleotide sequence set forth in SEQ ID NO: 6; the leukotoxin A ribosome binding site and start codon have the nucleotide sequence set forth in SEQ ID NO: 7; the added leukotoxin neutralizing epitope has the amino acid sequence set forth in SEQ ID NO: 9; the native leukotoxin A C-terminal amino acids have the sequence set forth in SEQ ID NO: 10; the RmAQP1 fragment has the amino acid sequence set forth in SEQ ID NO: 16; and the P2 epitope has the amino acid sequence set forth in SEQ ID NO: 14. In some embodiments of the invention, the polynucleotide encoding the added leukotoxin neutralizing epitope in the modified *M. haemolytica* lktCA gene cluster cassette has the nucleotide sequence set forth in SEQ ID NO: 8. In some embodiments of the invention, the polynucleotide encoding the RmAQP1 fragment in the modified *M. haemolytica* lktCA gene cluster cassette has the nucleotide sequence set forth in SEQ ID NO: 17. In some embodiments of the invention, the polynucleotide encoding the P2 epitope in the modified *M. haemolytica* lktCA gene cluster cassette has the nucleotide sequence set forth in SEQ ID NO: 15. In some embodiments, the modified *M. haemolytica* lktCA gene cluster cassette of the invention has the nucleic acid sequence set forth in SEQ ID NO: 18. In some embodiments, the modified *M. haemolytica* lktCA gene cluster cassette of the invention encodes an amino acid sequence set forth in SEQ ID NO: 19.

In an embodiment, the invention relates to a composition comprising a modified *M. haemolytica* lktCA gene cluster cassette, where the cassette comprises an insertion of a polynucleotide encoding an additional leukotoxin neutralizing epitope and at least one copy of a tick AQP1 fragment, wherein the polynucleotide is inserted downstream of the native leukotoxin A start codon. In some embodiments of the invention, the composition comprising the modified *M. haemolytica* lktCA gene cluster cassette of the invention is a polynucleotide, a plasmid, an expression vector, a host cell, a vaccine, or an immunogenic composition. In some embodiments of the invention, the composition comprising the modified *M. haemolytica* lktCA gene cluster cassette of the invention is a replacement plasmid, an attenuated *M. haemolytica* strain A1 bacteria, or an attenuated *M. haemolytica* strain A6 bacteria.

In an embodiment, the invention relates to a vaccine or immunogenic composition comprising a modified *M. haemolytica* lktCA gene cluster cassette, where the cassette comprises an insertion of a polynucleotide encoding an additional leukotoxin neutralizing epitope and at least one copy of a tick AQP1 fragment, wherein the polynucleotide is inserted downstream of the native leukotoxin A start codon or an *R. microplus* AQP1 fragment having the amino acid sequence set forth in SEQ ID NO: 16. The vaccine or immunogenic composition optionally comprises an adjuvant.

In an embodiment, the invention relates to a method of provoking an immune response in an animal, comprising administering to the animal at least one dose of a composition comprising a modified *M. haemolytica* lktCA gene cluster cassette, where the cassette comprises an insertion of a polynucleotide encoding an additional leukotoxin neutralizing epitope and at least one copy of a tick AQP1 fragment, wherein the polynucleotide is inserted downstream of the native leukotoxin A start codon, or an *R. microplus* AQP1 fragment having the amino acid sequence set forth in SEQ ID NO: 16. The composition optionally comprises an adjuvant. In some embodiments of the invention, the animal to which an immune response is provoked using a composition of the invention is a mammal. In some embodiments of the invention, the mammal to which an immune response is provoked is cow, a bull, a steer, a heifer, a sheep, a goat, a pig, a bison, an elk, a camel, a dog, or a deer. In some embodiments of the invention, the composition comprising a modified *M. haemolytica* lktCA gene cluster cassette of the invention is administered orally, nasally, enterally, parenterally, intramuscularly, intravenously, subcutaneously, intradermally, rectally, vaginally, topically, ocularly, pulmonarily, or by contact application.

16. A vaccine or immunogenic composition comprising the modified *M. haemolytica* lktCA gene cluster cassette of claim 1, or an *R. microplus* AQP1 fragment having the amino acid sequence set forth in SEQ ID NO: 16, and optionally an adjuvant.

In an embodiment, the invention relates to a kit comprising a modified *M. haemolytica* lktCA gene cluster cassette comprising an insertion of a polynucleotide encoding an additional leukotoxin neutralizing epitope and at least one copy of a tick AQP1 fragment inserted downstream of the native leukotoxin A start codon. In some embodiments of the invention, the kit comprises a composition comprising a modified *M. haemolytica* lktCA gene cluster cassette comprising an insertion of a polynucleotide encoding an additional leukotoxin neutralizing epitope and at least one copy of a tick AQP1 fragment, wherein the polynucleotide is inserted downstream of the native leukotoxin A start codon. In some embodiments of the invention the tick AQP1 fragment is a *R. microplus* AQP1 fragment.

BRIEF DESCRIPTION OF THE DRAWINGS

FIG. 4A shows the results obtained with AQP1 antibody. FIG. 4B shows the results obtained with anti-leukotoxoid antibody. The Y axis presents the antibody response calculated as the measured raw Optical Density (OD) minus the measured OD for a blank sample. The X axis presents the days following initial vaccination.

BRIEF DESCRIPTION OF THE SEQUENCE LISTING

Figure 1:
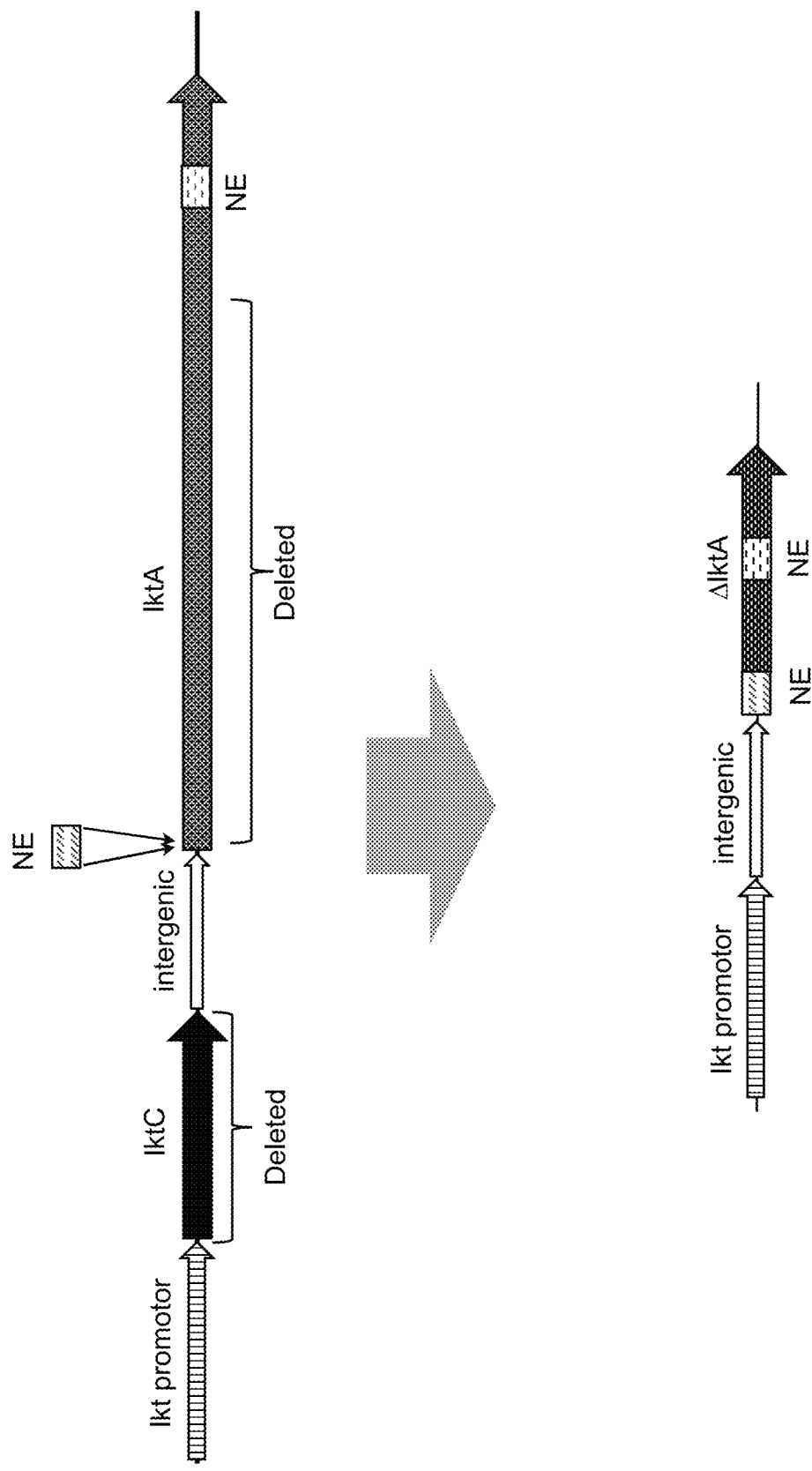
FIG. 1 depicts a schematic of the generation of *M. haemolytica* ΔlktCAV4 cassette. The leukotoxin lktCA gene cluster is depicted on the upper portion of the figure, as is the polynucleotide encoding the leukotoxin neutralizing epitope to be added. Portions of the lktCA gene cluster to be deleted to generate the ΔlktCAV4 cassette are shown bracketed. The *M. haemolytica* ΔlktCAV4 cassette is depicted on the lower portion of the figure. The leukotoxin promotor is shown by an arrow with vertical stripes; the leukotoxin C gene is shown by a black arrow; the lktC-lktA intergenic region (leukotoxin A ribosome binding site and start codon) is shown by a white arrow; the leukotoxin A gene is shown by a dotted arrow with the polynucleotide encoding the leukotoxin neutralizing epitope (NE) shown by alternating dashes; and the polynucleotide encoding the added NE is shown by stripes of back dashes.

The nucleotide and amino acid sequences disclosed in the specification are listed in Table 1, below.

| Sequence Identifier | Type | Description |
| --- | --- | --- |
| SEQ ID NO: 1 | nucleotide | *M. haemolytica* lktCA gene cluster |
| SEQ ID NO: 2 | nucleotide | down replacement arm |
| SEQ ID NO: 3 | nucleotide | down arm forward primer TM56 |
| SEQ ID NO: 4 | nucleotide | down arm reverse primer TM57 |
| SEQ ID NO: 5 | nucleotide | up replacement arm |
| SEQ ID NO: 6 | nucleotide | leukotoxin promotor |
| SEQ ID NO: 7 | nucleotide | lktC-lktA intergenic region |
| SEQ ID NO: 8 | nucleotide | leukotoxin neutralizing epitope codon-optimized sequence |
| SEQ ID NO: 9 | amino acid | added leukotoxin neutralizing epitope |
| SEQ ID NO: 10 | nucleotide | leukotoxin A nucleotides 2192 to 3022 |
| SEQ ID NO: 11 | amino acid | translation of leukotoxin A after nucleotide 2192 |
| SEQ ID NO: 12 | nucleotide | ΔlktCAV4 cassette |
| SEQ ID NO: 13 | amino acid | ΔlktCAV4 cassette |
| SEQ ID NO: 14 | amino acid | Tetanus Toxin P2 epitope (P2 Epitope) |
| SEQ ID NO: 15 | nucleotide | Codon-optimized sequence encoding P2 Epitope |
| SEQ ID NO: 16 | amino acid | RmAQP1 fragment |
| SEQ ID NO: 17 | nucleotide | Codon-optimized sequence encoding RmAQP1 fragment |
| SEQ ID NO: 18 | nucleotide | P2P2AQP1fAQP1fΔlktCAV4 cassette |
| SEQ ID NO: 19 | amino acid | P2P2AQP1fAQP1fΔlktCAV4 cassette |
| SEQ ID NO: 20 | amino acid | labeled AQP1 peptide |
| SEQ ID NO: 21 | amino acid | labeled Lkt peptide |

DETAILED DESCRIPTION

The inventors have inserted a polynucleotide encoding a chimeric peptide comprising a tandem repeat of a P2 epitope and of a portion of an RmAQP1 protein in a modified *M. haemolytica* lktCA gene cluster cassette comprising a polynucleotide encoding an added leukotoxin neutralizing epitope inserted downstream of the native leukotoxin A ribosome binding site and start codon. They have named the resulting polynucleotide P2P2AQP1fAQP1f-ΔlktCAV4 cassette. The inventors have prepared a vaccine using the chimeric polypeptide expressed by this cassette, and successfully used it to reduce tick infestation in cattle.

*M. haemolytica* is a gram-negative bacterium which is part of the normal nasal-pharyngeal flora of cattle, sheep, and goats. Under stress and/or concurrent respiratory infection, *M. haemolytica* can gain access to the lungs and cause fibrinous pneumonia. When compared to the wild-type parent, *M. haemolytica* possessing inactive leukotoxin are attenuated and elicit greatly reduced lung damage following experimental pulmonary challenge. Yet such modified strains retain the capacity to colonize the upper respiratory tract of cattle (Tatum F M et al., 1998, "*Construction of an isogenic leukotoxin deletion modified of Pasteurella haemolytica serotype 1: characterization and virulence*," Microb. Pathog. 24: 37-46). Moreover, cattle vaccinated mucosally with such defined *M. haemolytica* modified strains expressing and secreting inactive, yet immunogenic, leukotoxin (leuko-toxoid) are capable of generating neutralizing antibodies to leukotoxin that afford them resistant to virulent challenge (Briggs R E et al., 2012, "*Mucosal and parenteral vaccination against pneumonic pasteurellosis in cattle with a modified-live in frame lktA deletion modified of Mannheimia haemolytica*," Microb. Pathog. 52: 302-309).

The leukotoxin (lkt) operon of *M. haemolytica* codes for four proteins: an internal acyltransferase encoded by lktC; the structural toxin encoded by lktA; an inner membrane protein encoded by lktB; and a membrane fusion protein encoded by lktD. The genes for these four proteins are physically adjacent on the chromosome and are transcribed as lktCA or lktCABD messages.

U.S. Pat. No. 6,331,303, issued Dec. 18, 2001, discloses *P. haemolytica* bacterium which expresses no biologically active leukotoxin, expresses a leukotoxin molecule lacking amino acids 34 to 378, and contains no foreign DNA. In 1999, *P. haemolytica* was renamed as *Mannheimia haemolytica*.

US Patent Publication No. 2014/0170190 discloses a modified *M. haemolytica* strain A1 lktCA gene cluster with a deletion of a polynucleotide fragment consisting of the nucleotides encoding amino acid 4 of leukotoxin C to amino acid 707 of leukotoxin A, and replacement of the native leukotoxin C ribosome binding site (rbs) with an *E. coli* consensus rbs to generate D153ΔlktCA4-707rbs. The mutated lktCA gene cluster was introduced into wild-type *M. haemolytica* strains A1 and A6, resulting in attenuated bacteria. The attenuated *M. haemolytica* A1 and A6 strains were lyophilized, resuspended, and administered intranasally to calves aged 5 to 6 weeks. When administered intranasally, the mixture of attenuated *M. haemolytica* A1 and A6 strains containing D153ΔlktCA4-707rbs afforded protection to *M. haemolytica* challenge. When challenged with *M. haemolytica* A1 strain, nasal administration of *M. haemolytica* A1 and A6 strains containing D153ΔlktCA4-707rbs afforded an average reduction in lung lesion of 62.0% and 76.7% when compared to sham-inoculated cattle. When challenged with *M. haemolytica* A6 strain, nasal administration of *M. haemolytica* A1 and A6 strains containing D153ΔlktCA4-707rbs afforded an average reduction in lung lesion of 85.04% and 14.7% when compared to sham-inoculated cattle. U.S. Pat. No. 9,370,561, issued Jun. 21, 2016 from US Patent Publication No. 2014/0170190, and claims a vaccine comprising live, attenuated *M. haemolytica* A1 and A6 strains containing nucleic acid deletions in their respective leukotoxin A genes, that provide protective immune response against disease caused by *M. haemolytica* strains A1 and A6.

US Patent Application Publication 2019/0381161 discloses an oral vaccine against ruminant respiratory disease, comprising live attenuated *M. haemolytica* bacteria and a Polyvinylpyrrolidone (PVP). PVP enhances vaccination by oral route via drink.

At least 13 AQP members have been identified so far and classed into two subsets: those permeated by water and those permeated by water plus other small molecules, such as glycerol and urea. AQP structures are conserved among species, having six transmembrane domains that are connected by two intracellular loops and three extracellular loops. Two asparagine-proline-alanine (NPA) motifs are considered AQP signature motifs and are located at the protein portions that interact to form a pore.

In silico analyses of the tick AQP1 has identified peptide motifs that are said to be unique to tick AQP1 (Nedekezi C. et al., 2019, "*Identification of Ixodid Tick-Specific Aquaporin-1 Potential Anti-tick Vaccine Epitopes: An in-silico Analysis*," Front. Bioeng. Biotechnol. 7: 236). Based on multiple sequence alignment, motif analyses, homology modeling, and structural analyses, tick-specific AQP1 peptide motifs were said to be identified. Prediction modeling was used to predict the potential of these motifs to induce B cell-mediated immune responses. Two motifs on the tick AQP1 having GenBank ID QD067142.1 were identified, a motif named M7 comprised residues 106 to 125; and a motif named M8 comprised residues 85 to 104.

Use of bacterial vectors as vehicles to deliver recombinant antigens emerged in the late 1990s. Bacteria-based antigen delivery vectors exhibit multiple advantages, such as the possibility to control its intrinsic infectious power, its non-integrative properties, ability to regulate the amount and in vivo localization of the antigen, a potential for multiple vaccine delivery routes, potent stimulation of the innate and adaptive immune systems, and relatively low manufacturing costs. Bacterial vectors most frequently used as vaccine vectors are *Listeria* and *Salmonella*. Other attenuated bacteria used to express heterologous antigens, are *Pseudomonas aeruginosa*, *Mycobacterium bovis* (*Bacillus* Calmette-Guerin), *Vibrio anguillarum*, and *Vibrio V. cholera* (see review by Ding, C. al., "*Live Bacterial Vaccine Vector and Delivery Strategies of Heterologous Antigen: A Review*," 2018, Immunology Letters 197: 70-77).

Selected T cell epitopes from tetanus toxoid (TT) have been extensively studied. They have been shown to be widely recognized in association with a large number of major histocompatibility complex (MHC) class II molecules and to be universally immunogenic in humans and mice (Kaumaya P T, et al, 1993, "*Peptide vaccines incorporating a 'promiscuous' T-cell epitope bypass certain haplotype restricted immune responses and provide broad spectrum immunogenicity*," J. Mol. Recognit. 6(2):81-94). The tetanus toxin epitope P2 (830-843) has been used as antigen to bind major histocompatibility receptors on T cells, and to enhance the overall immune response. The amino acid sequence of the tetanus toxin epitope P2 is QYIKANSK-FIGITEL (set forth in SEQ ID NO: 14). This epitope has been demonstrated to facilitate B and T cell activation as well as proliferation in a number of mammalian species, but its effect in ruminants has not yet been evaluated.

The instant disclosure relates to a polynucleotide encoding at least one tick aquaporin fragment and at least one toxin epitope P2. Prior to the instant application, the effect of a P2 epitope on B and T cell activation in a ruminant was not known. The possible immunogenic response by ruminants to a chimera comprising a tick aquaporin 1 (AQP1) fragment and a tetanus toxin epitope 2 was also not known prior to the instant application. In an embodiment, the invention relates to a polynucleotide encoding an AQP1 fragment/P2 epitope chimera. In some embodiments of the invention, the polynucleotide encodes one copy of the AQP1 fragment. In some embodiments of the invention, the polynucleotide encodes two copies of the AQP1 fragment. In some embodiments of the invention, the polynucleotide encoding the RmAQP1 fragment has the nucleotide sequence set forth in SEQ ID NO: 17. In some embodiments of the invention, the polynucleotide encoding the P2 epitope has the nucleotide sequence set forth in SEQ ID NO: 15.

The instant disclosure relates to a modified *M. haemolytica* lktCA gene cluster cassette comprising a polynucleotide encoding an added leukotoxin neutralizing epitope and at least one copy of a tick AQP1 fragment inserted downstream of the leukotoxin A ribosome binding site and start codon. Prior to the present disclosure, expression of tick aquaporin fragments using a modified *M. haemolytica* lktCA gene cluster was not known. Prior to the instant application, it was not known if a modified *M. haemolytica* lktCA gene cluster cassette comprising at least one copy of a tick AQP1 fragment would be useful for the preparation of compositions, vaccines, or immunogenic compositions for administration to animals.

Prior to the instant disclosure, it was not known whether administration of a vaccine comprising a modified *M. haemolytica* lktCA gene cluster cassette comprising a polynucleotide encoding an added neutralizing epitope and at least one copy of a tick AQP1 fragment inserted downstream of the lktA ribosome binding site and start codon would elicit an immune response in an animal.

Disclosed herein are modified lktCA gene cluster cassettes derived from D153 ltkCA gene cluster. The wild type lktCA gene cluster has the nucleotide sequence set forth in SEQ ID NO: 1. In an embodiment, the invention relates to a modified *M. haemolytica* lktCA gene cluster cassette comprising an insertion of a polynucleotide encoding an additional *M. haemolytica* leukotoxin neutralizing epitope and at least one copy of a tick AQP1 fragment, where the polynucleotide is inserted downstream of the native leukotoxin A start codon. In some embodiments of the invention, the modified *M. haemolytica* lktCA gene cluster cassette comprises two copies of the tick AQP1 fragment. In some embodiments of the invention, the tick AQP1 fragment in the modified *M. haemolytica* lktCA gene cluster cassette is an *R. microplus* AQP1 (RmAQP1) fragment.

In an embodiment, the invention relates to a modified *M. haemolytica* lktCA gene cluster cassette comprising in a 5' to 3' orientation a leukotoxin promotor polynucleotide; a leukotoxin A ribosome binding site and start codon polynucleotide; a polynucleotide encoding an added leukotoxin neutralizing epitope; a polynucleotide encoding at least one copy of a tick AQP1 fragment; and a polynucleotide encoding at least native leukotoxin A amino acids 732 to 953. In some embodiments of the invention, the modified *M. haemolytica* lktCA gene cluster cassette comprises a polynucleotide encoding one copy of the tetanus toxin P2 epitope. In some embodiments of the invention, the modified *M. haemolytica* lktCA gene cluster cassette comprises a polynucleotide encoding two copies of the P2 epitope. In some embodiments of the invention, the polynucleotide encoding the RmAQP1 fragment has the nucleotide sequence set forth in SEQ ID NO: 17. In some embodiments of the invention, the polynucleotide encoding the P2 epitope has the nucleotide sequence set forth in SEQ ID NO: 15.

In some embodiments, the modified *M. haemolytica* lktCA gene cluster cassette comprises a leukotoxin promotor having the nucleotide sequence set forth in SEQ ID NO: 6; a leukotoxin A ribosome binding site and start codon having the nucleotide sequence set forth in SEQ ID NO: 7; an added leukotoxin neutralizing epitope having the amino acid sequence set forth in SEQ ID NO: 9; native leukotoxin A fragment having the amino acid sequence set forth in SEQ ID NO: 10; an RmAQP1 fragment having the amino acid sequence set forth in SEQ ID NO: 16; and a P2 epitope having the amino acid sequence set forth in SEQ ID NO: 14. In some embodiments of the invention, the polynucleotide encoding the added leukotoxin neutralizing epitope in the modified *M. haemolytica* lktCA gene cluster cassette has the nucleotide sequence set forth in SEQ ID NO: 8. In some embodiments of the invention, the polynucleotide encoding the RmAQP1 fragment in the modified *M. haemolytica* lktCA gene cluster cassette has the nucleotide sequence set forth in SEQ ID NO: 17. In some embodiments of the invention, the polynucleotide encoding the P2 epitope in the modified *M. haemolytica* lktCA gene cluster cassette has the nucleotide sequence set forth in SEQ ID NO: 15. In some embodiments, the modified *M. haemolytica* lktCA gene cluster cassette of the invention has the nucleotide sequence set forth in SEQ ID NO: 18. In some embodiments, the modified *M. haemolytica* lktCA gene cluster cassette of the invention encodes the amino acid sequence set forth in SEQ ID NO: 19.

The modified *M. haemolytica* lktCA gene cluster cassette of the invention, comprising a polynucleotide encoding two copies of the P2 epitope, and 2 copies of a tick AQP1 fragment protected calves against tick infestation challenge with at least 67% efficiency.

In some embodiments of the invention, the leukotoxin promotor, the lktA ribosome binding site and start codon, the polynucleotide encoding an added leukotoxin neutralizing epitope, and the polynucleotide encoding at least native leukotoxin A amino acids 732 to 953 are from *M. haemolytica* strain A1 or *M. haemolytica* strain A6.

In an embodiment, the invention relates to a composition comprising a modified *M. haemolytica* lktCA gene cluster cassette comprising a polynucleotide encoding an added leukotoxin neutralizing epitope and at least one copy of a tick AQP1 fragment. In some embodiments of the invention, the modified *M. haemolytica* lktCA gene cluster cassette further comprises a polynucleotide encoding one copy of a tetanus toxin P2 epitope. In some embodiments of the invention, the modified *M. haemolytica* lktCA gene cluster cassette comprises polynucleotides encoding two copies of the P2 epitope and two copies of the tick AQP1 fragment. In some embodiments of the invention, the tick AQP1 fragment in the modified *M. haemolytica* lktCA gene cluster cassette in an *R. microplus* AQP1 fragment. In some embodiments of the invention, the composition comprising a modified *M. haemolytica* lktCA gene cluster cassette of the invention is a polynucleotide, a plasmid, an expression vector, a host cell, a vaccine, or an immunogenic composition. In some embodiments of the invention, the composition comprising a modified *M. haemolytica* lktCA gene cluster cassette of the invention is a replacement plasmid, an attenuated *M. haemolytica* strain A1 bacteria, or an attenuated *M. haemolytica* strain A6 bacteria. In some embodiments of the invention, the composition comprising a modified *M. haemolytica* lktCA gene cluster cassette comprising a polynucleotide encoding an added leukotoxin neutralizing epitope and a tick AQP1 fragment is a vaccine or immunogenic composition, and optionally comprises an adjuvant.

In an embodiment, the invention relates to a modified *M. haemolytica* lktCA gene cluster cassette comprising a polynucleotide encoding an added leukotoxin neutralizing epitope, two copies of a RmAQP1 fragment, and two copies of a P2 epitope. In some embodiments, the modified *M. haemolytica* lktCA gene cluster cassette of the invention is referred to as a P2P2AQP1fAQP1fΔlktCAV4 cassette. In some embodiments, the invention relates to at least one plasmid comprising the P2P2AQP1fAQP1fΔlktCAV4 cassette. In some embodiments of the invention, the at least one plasmid is a replacement plasmid. In some embodiments, the invention relates to at least one bacteria comprising the P2P2AQP1fAQP1fΔlktCAV4 cassette.

In the modified *M. haemolytica* lktCA gene cluster cassette, deletion of lktC gene nucleotides −12 to 504 deletes the lktC ribosome binding site and the entire lktC coding region. Deletion of lktA gene nucleotides 4 through 2191 retains the lktC-lktA intergenic region including the lktA ribosome binding site and start codon, as well as lktA gene nucleotides 2192 to 3022, which include the polynucleotides encoding the leukotoxin glycine rich region and the leukotoxin neutralizing epitope. In some embodiments of the invention the modified lktCA gene cluster cassette contains added nucleotides corresponding to restriction endonuclease recognition sites. In some embodiments of the invention, the modified *M. haemolytica* lktCA gene cluster cassette of the invention contains added nucleotides corresponding to at least one EcoRI restriction endonuclease recognition site. In some embodiments of the invention, the modified *M. haemolytica* lktCA gene cluster cassette contains nucleotides corresponding to at least one MfeI restriction endonuclease recognition site. In some embodiments of the invention, the modified *M. haemolytica* lktCA gene cluster cassette contains nucleotides corresponding to at least one BamHI restriction endonuclease recognition site. At least one EcoRI, BamHI, or MfeI restriction endonuclease recognition site may be used to facilitate preparation of the modified *M. haemolytica* lktCA gene cluster cassette, its insertion into plasmids or vectors, or insertion of polynucleotides encoding heterologous antigens into the modified *M. haemolytica* lktCA gene cluster cassette.

Vaccines that provide consistent and efficacious protection against *R. microplus*, and that may be produced in useful quantities are desperately needed.

In the instant application, a polynucleotide encoding P2 epitope antigens and AQP1 antigens was inserted in a modified *M. haemolytica* lktCA gene cluster cassette. A polynucleotide encoding a chimeric antigen comprising two copies of the P2 epitope and two copies of an AQP1 fragment was introduced into the ΔlktCAV4 modified *M. haemolytica* lktCA gene cluster cassette to generate P2P2AQP1AQP1ΔlktCAV4 cassette. This cassette was introduced into a bacterial plasmid, transformed for expression in a laboratory strain of *E. coli*, where the resulting protein was isolated and used as vaccine product.

In an embodiment, the invention provides vaccines and immunogenic compositions that, when administered to a subject, elicit an immune response to *M. haemolytica* and/or *R. microplus* in the subject, e.g., a protective immune response. Methods of using the immunogenic compositions/vaccines to prevent or attenuate the spread of *R. microplus* and/or *M. haemolytica* infection in susceptible individuals and/or groups of susceptible individuals are also provided.

The vaccines or immunogenic compositions provided herein can be in the form of modified *M. haemolytica* lktCA gene cluster cassettes comprising P2 epitope and AQP1 antigens, as plasmids, or as vectors or bacteria expressing such cassettes. In some embodiments of the invention, the cassettes involved in evoking an immune response to *R. microplus* encode at least a fragment of Rm AQP1. In some embodiments of the invention, the cassettes involved in evoking an immune response to *R. microplus* encode at least a fragment of tetanus toxin P2 epitope. The immunogenic compositions/vaccines provided herein can be used to immunize or treat any mammal, including, but not limited to, cattle, sheep, goats, pigs, bison, elk, camels, dogs, and deer.

In an embodiment, the invention is directed at a vaccine to control *R. microplus* tick infestation, particularly in bison, beef, and dairy cattle. The vaccine may be used for injectable, intra-nasal, or oral delivery to the recipient animal, and may be combined with other vaccine components such as *Pasteurella multocida, Histophilus somni*, and/or viral components such as Bovine herpes virus 1 (BHV-1), parainfluenza virus type 3 (PI3V), and bovine respiratory syncytial virus (BRSV). Depending upon the selected delivery method, protection against *M. haemolytica* may be an intrinsic property of an *R. microplus* vaccine taught here.

In an embodiment, the invention relates to immunogenic compositions/vaccines that can be used to induce an immune response against *R. microplus*. In an embodiment, the invention relates to methods of administering a vaccine as described herein. The methods involve administering an effective amount of a vaccine sufficient to prevent or lessen the extent of *R. microplus* infestation in a subject, when the subject is later exposed to *R. microplus*.

In an embodiment, the invention relates to a vaccine to control *R. microplus* infestation, where the vaccine consists essentially of a modified *M. haemolytica* lktCA gene cluster cassette encoding *M. haemolytica* leuko-toxoid and a chimera encoding at least one copy of a P2 epitope and at least one copy of a tick AQP1 fragment. In some embodiments of the invention, the vaccine to control *R. microplus* comprises a modified *M. haemolytica* lktCA gene cluster cassette of the invention with an inserted recombinant polynucleotide encoding two copies of the P2 epitope and two copies of the tick AQP1 fragment. In some embodiments of the invention, the polynucleotide encoding the P2 epitope has the nucleotide sequence set forth in SEQ ID NO: 15. In some embodiments of the invention, the polynucleotide encoding the tick AQP1 fragment has the nucleotide sequence set forth in SEQ ID NO: 17. In some embodiments of the invention, the vaccine to control *R. microplus* infestation encodes a polypeptide having the amino acid sequence set forth in SEQ ID NO: 19. In some embodiments of the invention, the vaccine to control *R. microplus* infestation comprises bacteria with a modified *M. haemolytica* lktCA gene cluster cassette of the invention, comprising the recombinant polynucleotide of SEQ ID NO: 18.

In an embodiment, the invention provides methods for preparing a vaccine to control *R. microplus*. In some embodiments of the invention, such methods include using a modified *M. haemolytica* lktCA gene cluster cassette comprising a recombinant polynucleotide encoding a tick AQP1 fragment. In some embodiments of the invention, such methods include transforming bacteria with a polynucleotide comprising a modified *M. haemolytica* lktCA gene cluster cassette encoding a tick AQP1. Transformation can be achieved by any method known in the art, including, for example, electroporation or chemical transformation. A vaccine can be produced using an isolated nucleic acid to transform a bacterial culture. For example, a transformed bacterial culture can overexpress antigens to produce an immune response. In some embodiments, the vaccine to control *R. microplus* is prepared by inserting a recombinant polynucleotide encoding AQP1 into a modified *M. haemolytica* lktCA gene cluster cassette of the invention.

In some embodiments, a vaccine provided herein can include a marker of delivery and expression. For example, a polynucleotide encoding a P2 epitope/tick AQP1 fragment chimera may include a polynucleotide that encodes a fluorescent polypeptide (e.g., a green fluorescent protein, GFP). The fluorescent polypeptide will serve as a marker of expression and delivery of the vaccine to an animal. For example, a marker of delivery and expression can be detected e.g. as antibodies to the marker. For example, GFP antibodies may be detected in sera from immunized animals.

It is contemplated that virtually any nucleic acid sequence coding for an amino acid sequence that is or includes a P2 epitope/RmAQP1 fragment chimera may be used as described herein. This includes a polynucleotide encoding the amino acid sequence of any portion of the Rm AQP1 polypeptide. The amino acid sequences as described herein may also be shortened on either the amino or carboxy terminus (or both) by one, two, or more amino acids to produce fragments within the context of the invention wherein the fragments produce the same or a similar protective effect. Alternatively, the recombinant P2 epitope/RmAQP1 fragment polypeptide may be a chimera or fusion protein which comprises flanking amino acid sequences which are not adjacent to the native sequence in nature. For example, the adjacent sequences may be corresponding amino acids which are from different but related species; or amino acids which are from different species (e.g. from other bacteria or eukaryotes of interest, e.g. from infectious agents); or from a synthetic sequence, e.g. various tags such as histidine or glutathione S-transferase (GST) tags, linkers, spacers, targeting sequences, etc.).

Any effective route of administration may be utilized to deliver the vaccines of the invention, such as, for example, orally, nasally, enterally, parenterally, intramuscularly or intravenously, subcutaneously, intradermally, rectally, vaginally, topically, ocularly, pulmonarily, or by contact application. From a practical standpoint, oral, (intra)nasal, parenteral (IM, SubQ, and perhaps intradermal), and ocular may be preferred. In some embodiments, vaccine compositions of the invention may be injected (e.g., via intramuscular, intraperitoneal, intradermal and/or subcutaneous routes); or delivered via the mucosa (e.g., to the oral/alimentary, respiratory, and/or genitourinary tracts). Intranasal administration of vaccines may be particularly useful in some contexts, for example for treatment of pneumonia or otitis media (as nasopharyngeal carriage of pneumococci can be more effectively prevented, thus attenuating infection at its earliest stage). In some embodiments of the invention, it may be desirable to administer different doses of a vaccine by different routes. The vaccines provided herein can be administered using any appropriate method. Administration can be, for example, topical (e.g. transdermal, ophthalmic or intranasal); pulmonary (e.g., by inhalation or insufflation or powders or aerosols); oral, or parenteral (e.g. by subcutaneous, intrathecal, intraventricular, intramuscular, or intraperitoneal injection, or by intravenous drip). Administration can be rapid (e.g., by injection) or can occur over a period of time (e.g., by slow infusion or administration of slow release formulations). In some embodiments, the mode of administration is intraperitoneal. For application in livestock, the preferred mode of administration is oral.

Vaccine compositions are administered in such amounts and for such time as is necessary to achieve a desired result. As used herein, an "immunogenic" amount of the vaccine composition is an amount which is suitable to elicit an immune response. Thus, the amount effective to treat, attenuate, or prevent disease, as used herein, refers to a nontoxic but sufficient amount of the vaccine composition to treat, attenuate, or prevent disease in any subject. For example, the "therapeutically effective amount" can be an amount to treat, attenuate, or prevent infestation (e.g., tick infestation, R. microplus infestation), etc. The exact amount required to achieve an "immunogenic amount" may vary, depending on the particular component (e.g., polysaccharide, conjugate), and from subject to subject, depending on the species, age, and general condition of the subject, the stage of the disease, the particular pharmaceutical mixture, its mode of administration, and the like.

The amount of Rm AQP1 antigen or modified M. haemolytica lktCA gene cluster cassette carrying the RM AQP1 antigen in each vaccine dose is selected to allow the vaccine, when administered as described herein, to induce an appropriate immunoprotective response without significant adverse side effects. An "immuno-protective" or "protective immune" response as used herein is an immune response sufficient to protect an immunized subject from productive infection by a particular pathogen or pathogens to which a vaccine is directed (e.g., R. microplus infestation). Optimal amounts of components for a particular vaccine can be ascertained by standard studies involving observation of appropriate immune responses in subjects. Following an initial vaccination, subjects can receive one or several booster immunizations adequately spaced in time. Such amounts may vary depending upon which antigen or antigens are expressed by the modified M. haemolytica lktCA gene cluster cassette and/or preparations thereof, and may be formulated in a unit dosage form for ease of administration and uniformity of dosage. The expression "unit dosage form," as used herein, refers to a physically discrete unit of vaccine composition appropriate for the patient to be treated. The specific therapeutically effective dose for any particular patient or organism may depend upon a variety of factors including the severity or degree of risk of infection; the activity of the specific vaccine or vaccine composition employed; other characteristics of the specific vaccine or vaccine composition employed; the age, body weight, general health, sex of the subject, the diet of the subject, the pharmacokinetic condition of the subject, the time of administration (e.g., with regard to other activities of the subject such as eating, sleeping, receiving other medicines including other vaccine doses, etc.), the route of administration, the rate of excretion of the specific vaccine or vaccine composition employed; vaccines used in combination or coincidental with the vaccine composition employed; and like factors well known in the veterinary arts.

R. microplus vaccines for use in accordance with the present invention may be formulated according to known techniques. An immunogenic amount of a vaccine product can be formulated together with one or more pharmaceutically acceptable carrier materials (organic, inorganic, liquid, or solid). In general, pharmaceutically acceptable carriers include solvents, dispersion media, and the like, which are compatible with pharmaceutical administration. For example, materials that can serve as pharmaceutically acceptable carriers include, but are not limited to sugars such as lactose, glucose, dextrose, and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; polyols such as glycerol, propylene glycol, and liquid polyethylene glycol; esters such as ethyl oleate and ethyl laurate; agar; buffering agents such as magnesium hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as preservatives, and antioxidants can also be present in the composition, according to the judgment of the formulator (see also Remington's Pharmaceutical Sciences, Fifteenth Edition, E. W. martin (Mack Publishing Co., Easton Pa., 1975).

Vaccines of the present invention can further comprise one or more additional immunomodulatory components such as, e.g., an adjuvant or cytokine, among others. Non-limiting examples of adjuvants that can be used in the vaccine of the present invention include the RIBI adjuvant system (Ribi Inc., Hamilton, Montana, USA), alum, mineral gels such as aluminum hydroxide gel, oil-in-water emulsions, water-in-oil emulsions such as, e.g., Freund's complete and incomplete adjuvants, Block copolymer (CytRx, Atlanta, Georgia, USA), QS-21 (Cambridge Biotech Inc., Cambridge Massachusetts, USA), SAF-M (Chiron, Emeryville California, USA), AMPHIGEN, proprietary oil in water adjuvant (Zoetis, Parsippany, New Jersey, USA), saponin, Quil A (Brenntag Biosector A/S, Ballerup, Denmark), or other saponin fraction, monophosphoryl lipid A, and Avridine lipid-amine adjuvant. Other immunomodulatory agents that can be included in the vaccine of the invention, comprise, e.g., one or more interleukins, interferons, or other known cytokines.

In some embodiments, at least one booster vaccine is administered after the initial administration of the vaccine of the invention. The booster vaccine may be identical to the vaccine that is initially used to vaccinate the subject. The booster vaccine may be administered as early as four weeks after initial vaccination. In some embodiments, the booster vaccine may be administered at least one year after initial vaccination.

The immunogenic response from the initial or booster vaccine may protect a naive subject from subsequent full-blown R. microplus infestation when exposed to R. microplus. Alternatively, administration of the initial or booster vaccine is used to provide treatment for an existing R. microplus infestation. The protective response either wholly or partially prevents or arrests the development of symptoms related to R. microplus infestation, in comparison to a non-vaccinated control organism, in which R. microplus infestation is not prevented.

Vaccines of the present invention can be formulated following accepted convention to include acceptable carriers for animals, including humans (if applicable), such as standard buffers, stabilizers, diluents, preservatives, and/or solubilizers, and can also be formulated to facilitate sustained release. Diluents include water, saline, dextrose, ethanol, glycerol, and the like. Additives for isotonicity include sodium chloride, dextrose, mannitol, sorbitol, and lactose, among others. Stabilizers include albumin, among others. Other suitable vaccine vehicles and additives, including those that are particularly useful in formulating modified live vaccines, are known or will be apparent to those skilled in the art. See, e.g., Remington's Pharmaceutical Science, 18th ed., 1990, Mack Publishing, which is incorporated herein by reference.

An effective amount of any of the vaccines described herein can be determined by conventional means, starting with a low dose of a polypeptide including the P2 epitope/ RmAQP1 fragment chimera, an M. haemolytica replacement plasmid comprising such chimera, or M. haemolytica bacteria expressing such chimera, and then increasing the dosage while monitoring the effects. An effective amount may be obtained after a single administration of a vaccine or after multiple administrations of a vaccine. Known factors can be taken into consideration when determining an optimal dose per animal. These include the presence of other drugs in the animal, the species, size, age, and general condition of the animal, and the like.

One method of detecting whether an adequate immune response has been achieved is to determine seroconversion and antibody titer in the animal after vaccination. The timing of vaccination and the number of boosters, if any, will preferably be determined by a veterinarian based on analysis of all relevant factors, some of which are described above.

Suitable doses for vaccines according to the practice of the present invention range generally from about $1 \times 10^7$ to about $1.6 \times 10^{10}$ CFU per dose, as may be determined by standard methods. In dairy operations there is an interest in vaccinating cattle as early as 1 day of age. At this very young age, a mucosal delivery route may be preferred. It is also of interest to target the beef segment where 6-8 month old calves are typical recipients of the vaccine.

The effective dose amount of virus, infectious RNA molecule, plasmid, or viral vector, of the present invention can be determined using known techniques, taking into account factors that can be determined by one of ordinary skill in the art such as the weight of the animal to be vaccinated. By way of example, vaccines may be delivered orally, parenterally, intradermally, subcutaneously, intramuscularly, intranasally or intravenously. Oral delivery may encompass, for example, adding the compositions to the feed or drink of the animals.

The present invention further provides methods for preparing a vaccine or immunogenic composition comprising a polynucleotide encoding a P2 epitope/RMAQP1 fragment chimeric polypeptide, or a chimeric P2 epitope/RMAQP1 fragment polypeptide, or a P2P2AQP1fAQP1fΔlktCAV4 cassette comprising a polynucleotide encoding a chimeric P2 epitope/RMAQP1 fragment polypeptide, or a replacement plasmid comprising such a cassette, or bacterial strains comprising such a cassette, or vaccines or immunogenic compositions comprising such a cassette.

The method for preparing such a vaccine may comprise combining an effective amount of a chimeric P2 epitope/ RMAQP1 fragment polypeptide, an M. haemolytica replacement plasmid comprising a chimeric P2 epitope/RMAQP1 fragment insert, or bacterial strains described herein, with a carrier acceptable for pharmaceutical or veterinary use.

Additional features and variations of the invention will be apparent to those skilled in the art from the entirety of this application, including the detailed description, and all such features are intended as aspects of the invention. Likewise, features of the invention described herein can be re-combined into additional embodiments that also are intended as aspects of the invention, irrespective of whether the combination of features is specifically mentioned above as an aspect or embodiment of the invention. Also, only such limitations which are described herein as critical to the invention should be viewed as such; variations of the invention lacking limitations which have not been described herein as critical are intended as aspects of the invention. It will be clear that the invention may be practiced otherwise than as particularly described in the foregoing description and examples. Numerous modifications and variations of the present invention are possible in light of the above teachings and, therefore, are within the scope of the invention.

The invention is directed at a vaccine to control R. microplus infestation, particularly in beef, dairy cattle, and deer. The vaccine is intended for injectable, intra-nasal, or oral delivery to the recipient animal and may be combined with other vaccine components such as Pasteurella multocida, Mycoplasma bovis, Histophilus somni, and/or viral components such as BHV-1, PI-3V, and BRSV. Depending upon the selected delivery method, protection against M. haemolytica may be an intrinsic property of a vaccine taught here.

The vaccine may be delivered as a polypeptide product as tested here, as a modified-live vectored product via an attenuated M. haemolytica vaccine strain, as a killed vaccine strain, as a subunit vaccine product, or as a DNA vaccine. The M. haemolytica replacement vector utilized here consists of a gene-knockout modified which targeted the leukotoxin operon. M. haemolytica which does not express an active leukotoxin is dramatically attenuated in lung tissue, but remains capable of colonizing the nasopharynx where it can elicit an immune response. Because leukotoxin itself is an important immunogen, the vaccine strain is designed to express an inactive but immunogenic form of the protein—a genetic toxoid. Within the modified leukotoxin operon was placed an MfeI restriction site specifically for cloning of DNA, allowing heterologous DNA (preferably encoding protective immunogenic epitopes) to be cloned and expressed as a fusion product with the leuko-toxoid. In this case, DNA encoding fragments of tetanus toxin P2 epitope and *R. microplus* were cloned in-frame into the MfeI restriction site.

Nucleotide sequences encoding the tetanus toxin P2 epitope and a tick AQP1 fragment were codon-optimized. DNA encoding the chimeric protein was synthesized by Blue Heron Biotech (Bothell, Washington, USA). The 5' end was designed with nucleotides corresponding to an MfeI restriction endonuclease recognition site, and the 3' end was designed with nucleotides corresponding to an EcoR1 restriction endonuclease recognition site to allow cloning into a replacement plasmid containing Mfe1 at the cloning site. After cloning, the resultant plasmid was utilized to generate modified *Mannheimia haemolytica* serotype 1 and serotype 6.

In some embodiments of the invention, a vaccine provided herein can be delivered as a prophylactic vaccine to reduce the risk of *R. microplus* infestation to occur. In some instances, a vaccine provided herein can reduce the risk of developing bovine babesiosis and/or anaplasmosis should an *R. microplus* infection occur.

Although mucosal vaccination and leukotoxin deficient *M. haemolytica* are known, inventors are aware of no *M. haemolytica* vectors successfully combining the concepts disclosed herein.

In an embodiment, the invention relates to a method for vaccinating an animal, comprising administering a vaccine of the invention to the animal. In some embodiments, the vaccine of the invention comprises a cassette of the invention and a pharmaceutically acceptable carrier, excipient, or vehicle. In some embodiments of the invention, the vaccinated animal is an even toed ungulate ruminant. The vaccinated animal may be a cattle, a sheep, a goat, a deer, a giraffe, an elk, or a bison.

In an embodiment, the invention relates to a kit for performing methods of eliciting or inducing an immunogenic or protective response against a tick infestation. In some embodiments of the invention, the kit comprises a modified *M. haemolytica* lktCA gene cluster vector comprising a polynucleotide encoding an added neutralizing epitope, two copies of a P2 epitope, and two copies of an RmAQP1 fragment inserted downstream of the lktC-lktA intergenic region, and upstream of lktA gene nucleotide 2192. In some embodiments of the invention, the kit comprises a polynucleotide encoding a polypeptide with the amino acid sequence set forth in SEQ ID NO: 18. In some embodiments of the invention, the kit comprises a polynucleotide with the nucleotide sequence set forth in SEQ ID NO: 19.

The terms "antigen," "antigenic region," and "immunogen," may be used interchangeably herein. As used herein, an antigen or immunogen, or epitope is generally a portion of a protein (e.g. a peptide or polypeptide). Antigen is a term used historically to designate an entity that is bound by an antibody, and also to designate the entity that induces the production of the antibody. More current usage limits the meaning of antigen to that entity bound by an antibody, while the word "immunogen" is used for the entity that induces antibody production. Where an entity discussed herein is both immunogenic and antigenic, reference to it as either an immunogen or antigen will typically be made according to its intended utility.

As used herein, an "antigen" or "immunogen" is a substance that induces a specific immune response in a host animal. The antigen may comprise a whole organism either killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

An "immunological response" to a composition or vaccine is the development in the host of a cellular and/or antibody-mediated immune response to a composition or vaccine of interest. Usually, an "immunological response" includes, but is not limited to, one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms and/or clinical disease signs normally displayed by an infected host, a quicker recovery time and/or a lowered viral titer in the infected host.

By "animal" is intended mammals, birds, and the like. Animal or host as used herein includes mammals and human. The animal may be selected from the group consisting of cattle, sheep, goats, pigs, bison, elk, camels, dogs, and deer. The term "animal" also includes an individual animal in all stages of development, including newborn, embryonic and fetal stages.

As used herein, the term "about" is defined as plus or minus ten percent of a recited value. For example, about 1.0 g means 0.9 g to 1.1 g.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

Embodiments of the present invention are shown and described herein. It will be obvious to those skilled in the art that such embodiments are provided by way of example only. Numerous variations, changes, and substitutions will occur to those skilled in the art without departing from the invention. Various alternatives to the embodiments of the invention described herein may be employed in practicing the invention. It is intended that the included claims define the scope of the invention and that methods and structures within the scope of these claims and their equivalents are covered thereby. All publications, patents, and patent applications mentioned in this specification are herein incorporated by reference to the same extent as if each individual publication, patent, or patent application was specifically and individually indicated to be incorporated by reference.

EXAMPLES

Having now generally described this invention, the same will be better understood by reference to certain specific examples, which are included herein only to further illustrate the invention and are not intended to limit the scope of the invention as defined by the claims.

Example 1

Construction Modified *M. haemolytica* lktCA Gene Cluster Cassette

A modified *M. haemolytica* lktCA gene cluster cassette with an insertion of a polynucleotide encoding an additional *M. haemolytica* leukotoxin neutralizing epitope was prepared.

The polynucleotide cassette was designed to delete parent chromosomal nucleotides from the beginning of the lktC ribosome binding site to the beginning of the lktA ribosome binding site, thereby removing the entire lktC coding region. A second deletion was designed in-frame with the lktA coding region to remove the nucleotides encoding amino acids 2 to 731. A synthetic codon-optimized polynucleotide encoding the leukotoxin neutralizing epitope, flanked upstream by a synthetic MfeI site and downstream by a synthetic BamH1 site, was inserted in-frame with the second deletion, thereby duplicating the neutralizing epitope in the encoded leukotoxoid product. A schematic of the preparation of the modified *M. haemolytica* lktCA gene cluster cassette is depicted on FIG. 1.

The nucleotide sequence of the wild-type *M. haemolytica* D153 lktCA gene cluster is: ttct cttttgctaaatagtgttggtaagtagtccccattttgcacaccaatcgttttcacct-tagcaaaatctgtatctttttttcgcaatgaaggcagcagag cttg-gaaagtaaggctcgctaaataatacttgtttcttacgtggttccgtaataccatacct-gaaattgcagcatcaaattgatttgattaggctt tggattaagctatcaaaaggttggctatggaatgtacaatttgcattcatctctttaca-gatagcatttgcaatatccacatcaaaaccgataattt ctcccttctcttcggtcattt-caaatggaggatagcttggctccatcacaaatttga-tatcttgtgcctgcgcagtaaccacacacccgaataaa agggtcaaaagtgattttcataaaaagtccctgtgattcattataaggattaccactt-taacgcagttacttcttaaaaaaagtcttcttttcataa agtttgttttatgtcata-caaacacatcaaattgagatgtagtttctcaatcctcttgattcctctatct-caaaaaaacaacccaaaagaaaaaga aaagtatatgttacattaatattacaatgtaattatttttgtttaatttccctacat-tttgtataactttaaaacactccttttctcttctgattatataaaag acaaaaaata-caatttaagctacaaaaaacaacaaaaaacaacaaaaaacacgacaataa-gatcgagtaatgattatattatgttataattttg acctaatttagaataattatcgagtgcaaattATGaatcaatcttatttaact-tactaggaaacattacttggctatggatgaactcctccctcc acaaagaatg-gagctgtgaactactagcacgcaatgtgattcctgcaattgaaaat-gaacaatatgctacttatagataacggtattccgat cgcttattgtagttgggcagatttaaaccttgagactgaggtgaaatatattaaggat-attaattcgttaacaccagaagaatggcagtctggtg acagacgctggattattgat-tgggtagcaccattcggacattctcaattactt-tataaaaaatgtgtcagaaatacccctgatatgatcgtcagat ctatacgcttttatccaaagcagaaagaattaggcaaaattgcctactt-taaaggaggtaaattagataaaaaaacagcaaaaaaacgttttga tacatat-caagaagagctggcaacagcacttaaaaatgaatttaattttat-taaaaaatagaaggagacatcccttATGggaactagacttac aacccatcaaatgggctaaaaaacactttaacggcaaccaaaagtggcttacat-aaagccggtcaatcattaacccaagccggcagttcttt aaaaactggggcaaaaaaattatcctctatattccccaaaattaccaatatgatact-gaacaaggtaatggtttacaggatttagtcaaagcg gccgaagagttggggatt-gaggtacaaagagaagaacgcaataatattgcaacagctcaaaccagtt-taggcacgattcaaaccgctattg gcttaactgagcgtggcattgtgttatccgctccacaaattgataaattgcta-cagaaaactaaagcaggccaagcattaggttctgccgaaa gcattgta-caaaatgcaaataaagccaaaactgtattatctggcattcaatctatttttaggctcagt-attggctggaatggatttagatgaggcct tacagaataacagcaacccaacatgctcttgctaaagctggcttggagctaacaaat-tcattaattgaaaatattgctaattcagtaaaaaacactt gacgaatttggt-gagcaaattagtcaatttggttcaaaactacaaaatatcaaaggcttagggactt-taggagacaaactcaaaaatatcggtg gacttgataaagctggccttggtttagatgttatctcagggctat-tatcgggcgcaacagctgcacttgtacttgcagataaaaatgcttcaaca gctaaaaaagtgggtgcggggttttgaattggcaaaccaagttgttggtaatattac-caaagccgtttcttcttacattttagcccaacgtgttgca gcaggtttatctt-caactgggcctgtggctgctttaattgcttctactgtttctcttgcgattagcccattag-catttgccggtattgccgataaattt aatcatgcaaaaagtttagagagttatgccgaacgcttttaaaaaattaggc-tatgacggagataatttattagcagaatatcagcggggaaca gggactattgatg-catcggttactgcaattaataccgcattggccgctat-tgctggtggtgtgtctgctgctgcagccggctcggttattgcttc accgattgccttattagtatctgggattaccggtgtaatttctacgattctgcaatat-tctaaacaagcaatgtttgagcacgttgcaaataaaattc ataacaaaat-tgtagaatgggaaaaaaataatcacggtaagaactactttgaaaatggttac-gatgcccgttatcttgcgaatttacaagataat atgaaattcttactgaacttaaacaaagagttacaggcagaacgtgtcatcgctat-tactcagcagcaatgggataacaacattggtgatttag ctggtattagccgtt-taggtgaaaaagtccttagtggtaaagcctatgtggatgcgttt-gaagaaggcaaacacattaaagccgataaattagt acagttggattcggcaaacggttattattgatgtgagtaat-tcgggtaaagcgaaaactcagcatatcttattcagaacgccattattgacgccg ggaacagagcatcgtgaacgcgtacaaacaggtaaatatgaatatattac-caagctcaatattaaccgtgtagatagctggaaaattacagat ggtgcagcaagttctaccttttgatttaactaacgttgttcagcgtattggtattgaatta-gacaatgctggaaatgtaactaaaaccaaagaaac aaaaattattgc-caaacttggtgaaggtgatgacaacgtatttgttggttctggtacgacggaaatt-gatggcggtgaaggttacgaccgagtt cactatagccgtggaaactatggtgctttaactattgatgcaaccaaaga-gaccgagcaaggtagttataccgtaaatcgtttcgtagaaacc ggtaaagcacta-cacgaagtgacttcaacccataccgcattagtgggcaaccgt-gaagaaaaaatagaatatcgtcatagcaataaccagc accatgccggttattacaccaaagatacctttgaaagctgttgaagaaattatcggta-catcacataacgatatctttaaaggtagtaagttcaat gatgcctttaacggtggt-gatggtgtcgatactattgacggtaacgacggcaatgaccgcttat-ttggtggtaaaggcgatgatattctcgatg gtgggaaatggtgatgattttatcgatggcggtaaaggcaacgacctatta-cacggtggcaagggcgatgatattttcgttcaccgtaaaggcg atggtaatgatat-tattaccgattctgacggcaatgataaattatcattctctgattcgaacttaaaagatt-taacatttgaaaaagttaaacataat cttgtcatcacgaatagcaaaaaagagaaagtgaccatt-caaaactggttccgagaggctgattttgctaaagaagtgcctaattataaagca actaaagatgagaaaatcgaagaaatcatcggtcaaaatggcgagcggatcacct-caaagcaagttgatgatcttatcgcaaaaggtaacg gcaaaattacccaagat-gagctatcaaaagttgttgataactatgaattgctcaaacat-agcaaaaatgtgacaaacagcttagataagttaat ctcatctgtaagtgcatttacctcgtctaatgattcgagaaatgtattagtggctc-caacttcaatgttggatcaaagtttatcttctctcaatttgct agagcagcttaattt-taatgattggcaactctatattgtttcacacattatagagttgccgttttattt-tataaaaggagacaatatggaagctaac catcaaaggaatgatcttggtttagttgccctcactatgttggcacaataccataatat-ttcgcttaatccgaa; and is set forth in SEQ ID NO: 1.

A Down-Replacement arm and an Up-Replacement arm were created to introduce the changes in the *M. haemolytica* lktCA gene cluster. The Down-Replacement arm was generated by amplifying a portion of the *M. haemolytica* D153 lktCA gene cluster using polymerase chain reaction (PCR). The Down-arm Forward primer TM56 (AAAGGATCCTT-TAACGGTGGTG AT; set forth in SEQ ID NO: 3) added nucleotides corresponding to a BamHI restriction endonuclease recognition site at the 5' end of the Down-replacement arm. The Down-arm Reverse primer TM57 (AAAGAAT-TCCGGATTAAGCGAAATATTATGGTATTGT; set forth in SEQ ID NO: 4) added nucleotides corresponding to an EcoRI restriction endonuclease recognition site at the 3' end of the Down-replacement arm. Thus, in a 5' to 3' orientation, the Down-Replacement arm contained nucleotides corresponding to a BamHI restriction endonuclease recognition site, followed by nucleotides 3530 to 4360 of the *M. haemolytica* D153 lktCA gene cluster of SEQ ID NO: 1, followed by nucleotides corresponding to an EcoRI restriction endonuclease recognition site. The nucleotide sequence of the amplified Down-replacement arm is: GGATCCTT-TAACGGTGGTGATGGTGTCGATACTAT-TGACGGTAAC GACGGCAATGACCGCTTAT-TTGGTGGTAAAGGCGATGATATTCTCGATGGTGGA AAT GGTGATGATTTTATC-GATGGCGGTAAAGGCAACGACCTATTA-CACGGTGGCAAGGG CGATGATATTTCGTT-CACCGTAAAGGCGATGGTAATGATATTATTACCGAT TCTGA CGGCAATGATAAATTATCATTCTCTGAT-TCGAACTTAAAAGATTTAACATTTGAAAA AGT-TAAACATAATCTTGTCAT-CACGAATAGCAAAAAAGAGAAAGTGACCATTCAAA ACTGGTTCCGAGAGGCTGAT-TTTGCTAAAGAAGTGCCTAAT-TATAAAGCAACTAAAG ATGAGAAAATCGAAGAAATCATCGGT-CAAAATGGCGAGCGGATCACCTCAAAGCAA GTT-GATGATCTTATCGCAAAAGGTAACGGCAAAAT-TACCCAAGATGAGCTATCAAA AGTTGTTGATAACTATGAATTGCTCAAACAT-AGCAAAAATGTGACAAACAGCTTAG ATAAGT-TAATCTCATCTGTAAGTGCATTTACCTCGTCTAAT-GATTCGAGAAATGTATT AGTGGCTCCAACTTCAATGTTGGATCAAAGTT-TATCTTCTCTTCAATTTGCTAGAGCA GCTTAATTTT-TAATGATTGGCAACTCTATATTGTTTCACACAT-TATAGAGTTGCCGTT TTATTTTATAAAAGGAGACAATATGGAAGCTAAC-CATCAAAGGAATGATCTTGGTTT AGTTGCCCTCAC-TATGTTGGCACAATACCATAATATTTCGCT-TAATCCGGAATTC; and is set forth in SEQ ID NO: 2. Plasmid PBCSKlktDown was generated by subjecting the amplified Down-replacement arm PCR product to digestion with restriction endonuclease enzymes EcoRI and BamHI. After purification of the digested product, it was inserted into the corresponding sites of the pBC SK(−) cloning vector (Stratagene California; La Jolla, California, USA).

The Up-Replacement arm was synthesized by Blue Heron Biotech (Bothell, Washington, USA). In a 5' to 3' orientation, the synthesized Up-Replacement arm contained nucleotides corresponding to a BamHI restriction endonuclease recognition site, followed by nucleotides 1 to 807 and 1325 to 1341 of the *M. haemolytica* D153 lktCA gene cluster nucleotide sequence set forth in SEQ ID NO: 1, followed by nucleotides corresponding to an MfeI restriction endonuclease recognition site, followed by a codon-optimized sequence encoding the added leukotoxin neutralizing epitope, followed by nucleotides corresponding to a BamHI restriction endonuclease recognition site. The nucleotide sequence of the synthesized Up-Replacement arm is: GGATCCGAAT-TCTCTTTTGCTAAATAGTGTTGGTAAGTAGTCCCAT-TTTGCACACC AATCGTTTTCACCT-TAGCAAAATCTGTATCTTTTTCGCAATGAAGGCAG CAGAGCTT GGAAAGTAAGGCTCGCTAAATAATACTTGTTTCT-TACGTGGTTCCGTAATACCCATA CCTGAAAT-TGCAGCATCAAATTGTTTTTGTTTAGGCTTTGGAT-TAAGCTATCAAAAG GTTGGCTATGGAATGTACAATTTGCATTCATCTCTT-TACAGATAGCATTTGCAATATC CACATCAAAACC-GATAATTTCTCCCTTCTCTTCGGTCATTTCAAATG-GAGGATAGCTT GGCTCCATCACAAATTTGA-TATCTTGTGCCTGCGCAGTAAC-CACACACCCGAATAAA AGGGT-CAAAAGTGTTTTTTTCATAAAAAGTCCCTGTGTTTT CATTATAAGGATTACCA CTTTAACGCAGT-TACTTTCTTAAAAAAAGTCTTCTTTTCAT-AAAGTTTGTTTTATGTC ATACAAACACATCAAATT-GAGATGTAGTTTCTCAATCCTCTTGATTCCTCTATCT-CAA AAAAACAACC-CAAAAGAAAAAAGAAAAGTATATGTTACATTAAT-ATTACAATGTAA TTATTTTGTTTAATTTCCCTACAT-TTTGTATAACTTTAAAACACTCCTTTTTCTCTTCT GATTATATAAAAGACAAAAAATACAATTTAAGCTA-CAAAAAACAACAAAAAACAAC AAAAAACACGACAATAAGATCGAGTAATGATTAT-ATTATGTTATAATTTTTGACCTA ATTTAGAATAAT-TATAGGAGACATCCCTTATGCAATTGGTAATTA-CAAATAGCAAAA AAGAAAAAGTAACAATTCAAAATTGGTTTCGT-GAAGCAGATTTCGCTAAAGAAGTT CCAAAT-TATAAAGCAACGAAGGATGAAAAAATT-GAAGAAATTATTGGACAAAATGG AGAACGTATTACAAGTAAACAAGTAGATGACT-TAATCGCAAAAGGTAACGGAAAAA TTACTCAG-GATGAATTATCGAAGGTGGTAGATAACTAT-GAAGGATCC; and is set forth in SEQ ID NO: 5. Plasmid pBCSKlktUp-Down was generated by inserting the synthetic Up-Replacement arm into BamH1-digested pBCSK-lktDown. The correct orientation of the Up-Replacement arm was determined using standard Sanger DNA sequencing (performed at the Iowa State University DNA facilities in Ames, Iowa, USA). The resulting pBCSKlktUp-Down plasmid contains the ΔlktCAV4 cassette.

A depiction of the modified lktCA gene cluster cassette is shown in FIG. 1. The top portion of the figure depicts the *M. haemolytica* leukotoxin lktCA gene cluster, which contains the lkt promotor (grey arrow); the lktC gene open reading frame (black arrow); the lktC-lktA intergenic region (white arrow); the lktA gene open reading frame (dotted arrow); the added lkt neutralizing epitope (NE, striped slashes), and brackets showing the sections of the lktCA gene cluster to be deleted. The lktA open reading frame includes nucleotides encoding the LktA glycine rich region (GRR, diagonal bricks) and the NE (alternating horizontal dashes). The bottom portion of the figure depicts the *M. haemolytica* ΔlktCAV4 cassette, which contains the lkt promotor (grey arrow); the lktC-lktA intergenic region (white arrow); the added lkt NE (striped slashes); and nucleotides encoding LktA amino acids 731 to 953 (ΔlktA, dotted arrow). ΔLktA comprises nucleotides encoding the LktA GRR (diagonal bricks) and NE (alternating horizontal dashes).

The nucleotide sequence of the native leukotoxin promotor region is: TTCTCTTTTGCT AAATAGTGTTGGTAAGTAGTCCCATTTTGCACAC-CAATCGTTTTCACCTTAGCAAAA TCTGTATCTTTTTCGCAAT-GAAGGCAGCAGAGCTTG-GAAAGTAAGGCTCGCTAAAT AATACTTGTTTCT-TACGTGGTTCCGTAATACCCATACCTGAAATTGCAG-CATCAAATT GTTTTTGTTTTAGGCTTTGGATTAAGCTAT-CAAAAGGTTGGCTATGGAATGTACAATT TGCATT-CATCTCTTTACAGATAGCATTTGCAATATCCACAT- CAAAACCGATAATTTCT CCCTTCTCTTCGGTCATTTCAAATGGAGGA-TAGCTTGGCTCCATCACAAATTTGATAT CTTGTGCCTGCGCAGTAAC-CACACACCCGAATAAAAGGGT-CAAAAGTGTTTTTTTCA TAAAAAGTCCCTGTGTTTTCATTATAAGGATTAC-CACTTTAACGCAGTTACTTTCTTA AAAAAAGTCTTCTTTTCATAAAGTTTGTTTTATGT-CATACAAACACATCAAATTGAG ATGTAGTTTCT-CAATCCTCTTGATTCCTCTATCT-CAAAAAAACAACCCAAAAGAAAA AAGAAAAGTATATGTTACATTAATATTA-CAATGTAATTATTTTGTTTAATTTCCCTAC ATTTTGTATAACTTTAAAACACTCCTTTTTCTCTTCT-GATTATATAAAAGACAAAAAA TACAATTTAAGCTA-CAAAAAAACAACAAAAAACAACAAAAAACACGAC AATAAGAT CGAGTAATGATTATATTATGTTATAAT-TTTTGACCTAATTTAGAATAATTAT; and is set forth in SEQ ID NO: 6. The sequence of the native lktC-lktA intergenic region is AAGGAGAC ATCCCTT; and is set forth in SEQ ID NO: 7.

The codon-optimized nucleotide sequence encoding the added leukotoxin neutralizing epitope is: CAATTGGTAAT-TACAAATAGCAAAAAAGAAAAAGTAACAATT-CAAAATT GGTTTCGTGAAGCAGAT-TTCGCTAAAGAAGTTCCAAATTATAAAGCAACGAA GGAT GAAAAAATTGAAGAAATTAT-TGGACAAAATGGAGAACGTATTA-CAAGTAAACAAGT AGATGACT-TAATCGCAAAAGGTAACGGAAAAATTACTCAGGAT GAATTATCGAAGG TGGTAGATAACTAT-GAAGGATCC; and is set forth in SEQ ID NO: 8. The amino acid sequence of the added leukotoxin neutralizing epitope is: QLVITNSKKEKVTIQNWFREAD FAKEV-PNYKATKDEKIEEIIGQNGERITSKQVDDLIAKGNG-KITQDELSKVVDNYEGS; and is set forth in SEQ ID NO: 9. The nucleotide sequence of lktA nucleotides 2192 to 3022 is: CCTTTAACGGTGGTGATGGTGTCGATACTAT-TGACGGTAACGACGGCAATGACCG CTTAT-TTGGTGGTAAAGGCGATGATATTCTCGATGGTG-GAAATGGTGATGATTTTAT CGATGGCGGTAAAGGCAACGACCTATTA-CACGGTGGCAAGGGCGATGATATTTTCG TTCACCGTAAAGGCGATGGTAATGATATTATTACC-GATTCTGACGGCAATGATAAAT TATCATTCTCTGAT-TCGAACTTAAAAGATTTAACATTTGAAAAAGT-TAAACATAATC TTGTCATCACGAATAGCAAAAAAGAGAAAGTGAC-CATTCAAAACTGGTTCCGAGAG GCTGAT-TTTGCTAAAGAAGTGCCTAAT-TATAAAGCAACTAAAGATGAGAAAATCGA AGAAATCATCGGTCAAAATGGCGAGCGGATCACCT-CAAAGCAAGTTGATGATCTTA TCGCAAAAGGTAACGGCAAAATTACCCAAGAT-GAGCTATCAAAAGTTGTTGATAAC TATGAATTGCT-CAAACATAGCAAAAATGTGACAAACAGCTTAGA-TAAGTTAATCTCA TCTGTAAGTGCATTTACCTCGTCTAATGAT-TCGAGAAATGTATTAGTGGCTCCAACTT CAATGTTGGATCAAAGTTTATCTTCTCTTCAAT-TTGCTAGAGCAGCTTAATTTTAAT GAT-TGGCAACTCTATATTGTTTCACACAT-TATAGAGTTGCCGTTTTATTTTATAAAG GAGACAATATGGAAGCTAACCATCAAAGGAAT-GATCTTGGTTTAGTTGCCCTCACTA TGTTGGCACAATACCATAATATTTCGCTTAATCCG-GAA; and is set forth in SEQ ID NO: 11.

The amino acid sequence of the polypeptide resulting from the translation of the M. haemolytica nucleotides 3' of the inserted heterologous polynucleotide is ELVITNSKKEKVTIQNWFREADFAKEV-PNYKATKDEKIEEIIGQNGERITSKQVDDLIAK GNG-KITQDELSKVVDNYEGSFNGGDGVDTIDGNDGN-DRLFGGKGDDILDGGNGDDFID GGKGNDLLHGGKGDDIFVHRKGDVKDLT-FEKVKHNLVITNSKKEKVTIQNWFREADFA KEV-PNYKATKDEKIEEIIGQNGERITSKQVDDLIAKGNG-KITQDELSKVVDNYELLKHSK NVTNSLDKLIS-SVSAFTSSNDSRNVLVAPTSMLDQSLSSLQFARAA*, and is set forth in SEQ ID NO: 10.

The nucleotide sequence of the M. haemolytica ΔlktCAV4 cassette is GAATTCTCTTTT GCTAAATAGTGTTGGTAAGTAGTCCCAT-TTTGCACACCAATCGTTTTCACCTTAGCA AAATCTGTATCTTTTTTCGCAAT-GAAGGCAGCAGAGCTTGGAAAGTAAGGCTCGCTA AATAATACTTGTTTCTTACGTGGTTCCGTAATACC-CATACCTGAAATTGCAGCATCA AATTGTTTTTGTTT-TAGGCTTTGGATTAAGCTATCAAAAGGTTGGC-TATGGAATGTAC AATTTGCATTCATCTCTTTACAGATAGCAT-TTGCAATATCCACATCAAAACCGATAA TTTCTCCCTTCTCTTCGGTCATTTCAAATGGAGGA-TAGCTTGGCTCCATCACAAATTT GATATCTTGTGCCTGCGCAGTAAC-CACACACCCGAATAAAAGGGTCAAAAGTGTTTT TTTCATAAAAAGTCCCTGTGTTTTCATTATAAGGAT-TACCACTTTAACGCAGTTACTT TCT-TAAAAAAAGTCTTCTTTTCATAAAGTTTGTTT-TATGTCATACAAACACATCAAAT TGAGATGTAGTTTCTCAATCCTCTTGATTCCTC-TATCTCAAAAAAACAACCCAAAAG AAAAAAGAAAAGTATATGTTACATTAATATTA-CAATGTAATTATTTTGTTTAATTTCC CTACAT-TTTGTATAACTTTAAAACACTCCTTTTTCTCTTCT-GATTATATAAAAGACAA AAAATACAATTTAAGCTA-CAAAAAACAACAAAAAACAACAAAAAACACGAC AATA AGATCGAGTAATGATTATATTATGTTATAAT-TTTTGACCTAATTTAGAATAATTATAG GAGA-CATCCCTTATGaattgGTAATTA-CAAATAGCAAAAAGAAAAAGTAACAATTCA AAATTGGTTTCGTGAAGCAGAT-TTCGCTAAAGAAGTTCCAAATTATAAAGCAACGA AGGATGAAAAAATTGAAGAAATTAT-TGGACAAAATGGAGAACGTATTACAAGTAAA CAAGTAGATGACTTAATCGCAAAAGGTAACG-GAAAAATTACTCAGGATGAATTATC GAAGGTGGTA-GATAACTATGAAggatccTTTAACGGTGGT-GATGGTGTCGATACTATTG ACGGTAACGACGGCAATGACCGCTTAT-TTGGTGGTAAAGGCGATGATATTCTCGATG GTG-GAAATGGTGATGATTTTATC-GATGGCGGTAAAGGCAACGACCTATTACACGGT GGCAAGGGCGATGATATTTTCGTT-CACCGTAAAGGCGATGGTAATGATATTATTACC GAT-TCTGACGGCAATGATAAATTATCATTCTCTGAT-TCGAACTTAAAAGATTTAACA TTTGAAAAAGTTAAACATAATCTTGTCAT-CACGAATAGCAAAAAAGAGAAAGTGAC CATT-CAAAACTGGTTCCGAGAGGCTGAT- TTTGCTAAAGAAGTGCCTAATTATAAAGC AACTAAAGATGAGAAAATCGAAGAAATCATCGGT-CAAAATGGCGAGCGGATCACCT CAAAGCAAGTT-GATGATCTTATCGCAAAAGGTAACGGCAAAAT-TACCCAAGATGAG CTATCAAAAGTTGTTGATAACTATGAATTGCT-CAAACATAGCAAAAATGTGACAAAC AGCTTAGA-TAAGTTAATCTCATCTGTAAGTGCATT-TACCTCGTCTAATGATTCGAGA AATGTATTAGTGGCTCCAACTTCAATGTTGGAT-CAAAGTTTATCTTCTCTTCAATTTG CTAGAGCAGCTTAATTTTTAATGATTGGCAACTC-TATATTGTTTCACACATTATAGAG TTGCCGTTTTAT-TTTATAAAAGGAGACAATATGGAAGCTAACCAT-CAAAGGAATGAT CTTGGTTTAGTTGCCCTCACTATGTTGGCACAATAC-CATAATATTTCGCTTAATCCGG AATTC; and it is set forth in SEQ ID NO: 12.

The amino acid sequence of the *M. haemolytica* ΔlktCAV4 cassette is MQLVITNSKKE KVTIQNWFREADFAKEVPNYKATKDEKIEE-IIGQNGERITSKQVDDLIAKGNGKITQDEL SKVVDNYEGSFNGGDGVDTIDGNDGN-DRLFGGKGDDILDGGNGDDFIDGGKGNDLLH GGKGDDIFVHRKGDGN-DIITDSDGNDKLSFSDSNLKDLT-FEKVKHNLVITNSKKEKVTIQ NWFREADFAKEV-PNYKATKDEKIEEIIGQNGERITSKQVDDLIAKGNGKI TQDELSKVVD NYELLKHSKNVTNSLDKLIS-SVSAFTSSNDSRNVLVAPTSMLDQSLSSLQFARAA*; and is set forth in SEQ ID NO: 13.

To add a selectable marker and a temperature-sensitive origin of replication, the *M. haemolytica* ΔlktCAV4 cassette was inserted in the plasmid pCT109GA189-Kan. Plasmid pCT109GA189-Kan (described in Briggs, R. E. and Tatum, F. M., 2005, "*Generation and Molecular Characterization of New Temperature-Sensitive Plasmids Intended for Genetic Engineering of Pasteurellaceae*," Appl. Environ. Microbiol. 71(11): 7187-7195) and plasmid pBCSKlktUp-Down were digested with restriction endonuclease enzyme XbaI, treated with Shrimp alkaline phosphatase, and ligated to each other to generate the replacement plasmid pBCΔlktCAV4-pCT109GA189-Kan.

To generate modified *M. haemolytica* D153 (serotype 1) and *M. haemolytica* D174 (serotype 6) bacteria containing the ΔlktCAV4 cassette, the replacement plasmid pBCΔlktCAV4-pCT109GA189-Kan was introduced into *M. haemolytica* D153 (serotype 1) and *M. haemolytica* D174 (serotype 6) using electroporation as described by Briggs, R. E., et al. ("*Characterization of a Restriction Endonuclease, PhaI, from Pasteurella haemolytica Serotype A1 and Protection of Heterologous DNA by a cloned Pha I methyltransferase gene,*" 1994, Appl. Environ. Microbiol. 60(6): 2006-2010) except that the replacement plasmid was not subjected to passage through *E. coli* strain PhaI Mtase. The two *M. haemolytica* strains transformed with the replacement plasmid were treated with the steps described in Tatum, F. M. and Briggs R. E. ("*Construction of In-Frame aroA Deletion Modifieds of Mannheimia haemolytica, Pasteurella multocida, and Haemophilus somnus by Using a New Temperature-Sensitive Plasmid,*" 2005, Appl. Environ. Microbiol. 71(11): 7196-7202) to generate the modified *M. haemolytica* modified products D153ΔlktCAV4 and D174ΔlktCAV4 containing the modified *M. haemolytica* lktCA cassette. These modified *M. haemolytica* strains D153ΔlktCAV4 and D174ΔlktCAV4 are useful as antigen-expression vectors, and as vaccine products.

Example 2

Generation of Anti-Tick Vaccine Product

A polynucleotide fragment encoding a chimeric protein comprising a tandem repeat of the P2 epitope and a tandem repeat of the RmAQP1 fragment was inserted into the unique MfeI restriction endonuclease recognition site of the *M. haemolytica* ΔlktCAV4 cassette to generate the P2P2AQP1fAQP1fΔlktCAV4 cassette.

The amino acid sequence of the tetanus toxin epitope P2 is QFQYIKANSKFIGITE; and is set forth in SEQ ID NO: 14. The codon-optimized nucleotide sequence of the tetanus toxin epitope P2 used to generate the P2P2AQP1fAQP1fΔlktCAV4 cassette is caattccaatacattaaagc aaattcaaaattcattggcattacggaa; and is set forth in SEQ ID NO: 15. The sequence of a 53 amino acid segment encompassing an RmAQP1 extracellular domain (RmAQP1f) used to generate the P2P2AQP1fAQP1fΔlktCAV4 cassette is LALVFATYK-DAIEHFDQGIRQVTGEKATAGIFAT YPRPHVSTLTC-FIDQVIAT; and is set forth in SEQ ID NO: 16. The codon-optimized nucleotide sequence of the RmAQP1f is ttggctttagtttttgcaacctacaaagatgctattgaacattttgatcagggta ttcgt-caagttacaggtgaaaaagcaaccgcaggtattttttgcaacctatcctcgtcca-catgtaagtactttaacttgttttattgatcaagtaatt gccact; and is set forth in SEQ ID NO: 17.

Polynucleotide fragments encoding tandem repeats of the P2 epitope and the AQP1 fragment were synthesized with nucleotides corresponding to MfeI and EcoR1 restriction enzyme recognition sites added at the 5' end and 3' end, respectively. The polynucleotide fragments encoding the P2 and AQP1 fragment tandem repeats were custom synthesized by Blue Heron Biotech (Bothel, Washington, USA). These P2 and AQP1 fragments were sequentially inserted into the MfeI site of the ΔlktCAV4 cassette using standard cloning procedures to generate the P2P2AQP1AQP1ΔlktCAV4 cassette. Each polynucleotide addition was confirmed by standard DNA sequencing. The nucleotide sequence of the P2P2AQP1AQP1ΔlktCAV4 cassette is caattccaatacattaaagcaaattcaaaattcattggcattacg-gaacaattccaatacattaaagcaaattcaaaattcattgg cattacggaacaat-tggctttagtttttgcaacctacaaagatgctattgaacattttgatcagggtattcgtca agttacaggtgaaaaagcaac cgcaggtattttttgcaacctatcctcgtcca-catgtaagtactttaacttgttttattgatcaagtaattgccactgaattggctt-tagtttttgcaacc tacaaagatgctattgaacattttgatcagggtattcgtcaagt-tacaggtgaaaaagcaaccgcaggtattttttgcaacctatcctcgtccacat gtaagtactttaacttgttttattgatcaagtaattgccactgaattggtaatta-caaatagcaaaaaagaaaaagtaacaattcaaaattggtttc gtgaagcagat-ttcgctaaagaagttccaaattataaagcaacgaaggatgaaaaaattgaagaaat-tattggacaaaatggagaacgtatta caagtaaacaagtagatgacttaatcgcaaaaggtaacggaaaaattactcaggat-gaattatcgaaggtggtagataactatgaaggatcct ttaacggtggt-gatggtgtcgatactattgacggtaacgacggcaatgaccgcttat-ttggtggtaaaggcgatgatattctcgatggtggaaa tggtgatgattttatcgatggcggtaaaggcaacgacctatta-cacggtggcaagggcgatgatattttcgttcaccgtaaaggcgatgtaaa agatt-taacatttgaaaaagttaaacataatcttgtcat-cacgaatagcaaaaaagagaaagtgaccattcaaaactggttccgagaggctgat tttgctaaagaagtgcctaattataaagcaactaaagatgagaaaatcgaagaaat-catcggtcaaaatggcgagcggatcacctcaaagca agttgatgatct-tatcgcaaaaggtaacggcaaaattacccaagatgagctatcaaaagttgttga-taactatgaattgctcaaacatagcaaa aatgtgacaaacagcttagataagttaatctcatctgtaagtgcatt-
tacctcgtctaatgattcgagaaatgtattagtggctccaacttcaatgtt ggat-
caaagtttatcttctcttcaatttgctagagcagcttaa; and is set forth in
SEQ ID NO: 18.

The P2P2AQP1AQP1ΔlktCAV4 cassette was amplified by PCR and inserted into the pet-Sumo protein expression system (Invitrogen Thermo Fisher Scientific; Waltham, Massachusetts, USA), and expressed in *E. coli* cells using standard cloning techniques. The protein expression levels were determined by Western blotting using an in-house-generated mouse monoclonal antibody specific to *M. haemolytica* leukotoxin. This monoclonal antibody binds to the leukotoxoid portion of the hybrid protein, and can be detected with labeled anti-mouse antibody. The amino acid sequence of the protein expressed by the P2P2AQP1AQP1ΔlktCAV4 cassette is QFQYIKANSK-FIGITEQFQYIKANSKFIGITEQLALV FATYK-DAIEHFDQGIRQVTGEKATAGIFATYPRPHVSTLTC-FIDQVIATELALVFATYKD
AIEHFDQGIRQVTGEKATAGIFATYPRPHVSTLTC-FIDQVIATELVITNSKKEKVTIQNWF READFAKEV-PNYKATKDEKIEEIIGQNGERITSKQVDDLIAKGNG-KITQDELSKVVDNYE
GSFNGGDGVDTIDGNDGNDRLFGGKGDDILDGG-NGDDFIDGGKGNDLLHGGKGDDIFV HRKGDVKDLT-FEKVKHNLVITNSKKEKVTIQNWFREADFAKEV-PNYKATKDEKIEEIIG
QNGERITSKQVDDLIAKGNGKITQDEL-SKVVDNYELLKHSKNVTNSLDKLISSVSAFTSS
NDSRNVLVAPTSMLDQSLSSLQFARAA*, and is set forth in SEQ ID NO: 19.

Upon expression, the recombinant product produced by the P2P2AQP1AQP1ΔlktCAV4 cassette was contained primarily in inclusion bodies. Purification of the recombinant peptide was accomplished using B-Per Reagent (Pierce, Rockford, Illinois, USA) according to the manufacturer's directions. The purified recombinant peptide was resuspended in phosphate buffered saline and quantitative estimations of protein concentration was assessed by comparing the recombinant preparations to bovine serum albumin standards run on SDS PAGE after coomassie blue staining, and by the "Bradford" protein assay (BioRad, Hercules, California, USA).

Figure 2:
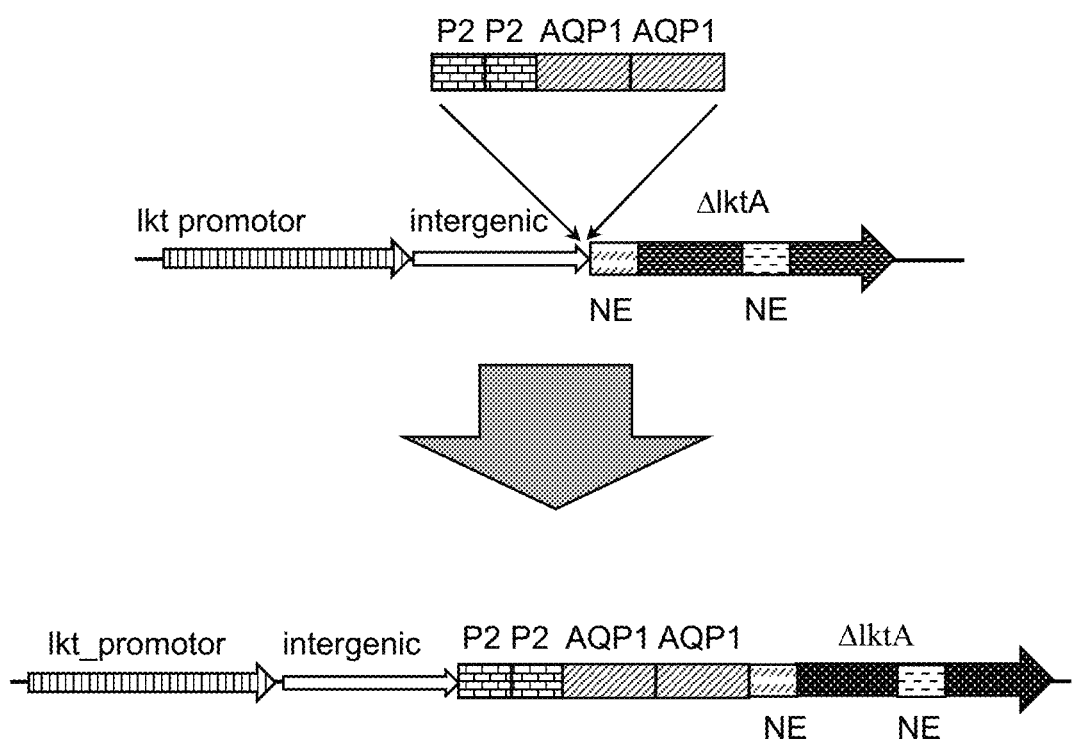
FIG. 2 depicts a schematic of the generation of the *M. haemolytica* ΔlktCAV4MBovis cassette from the *M. haemolytica* ΔlktCAV4 cassette. The *M. haemolytica* ΔlktCAV4 cassette is depicted on the upper portion of the figure, as is the polynucleotide encoding the added *M. bovis* EF-Tu/DnaK chimera. The *M. haemolytica* ΔlktCAV4MBovis cassette is depicted on the lower portion of the figure. The leukotoxin promotor is shown by an arrow with vertical stripes; the lktC-lktA intergenic region is shown by a white arrow; the polynucleotide encoding the added NE is shown by stripes of back dashes; the leukotoxin A gene portions present are shown by a dotted arrow; the polynucleotide encoding leukotoxin A NE is shown by alternating dashes; the polynucleotide encoding *M. bovis* EF-Tu is shown by horizontal bricks; and the polynucleotide encoding *M. bovis* DnaK is shown by diagonal stripes.

FIG. 2 depicts a schematic of the generation of the P2P2AQP1fAQP1fΔlktCAV4 cassette from the *M. haemolytica* ΔlktCAV4 cassette. The *M. haemolytica* ΔlktCAV4 cassette is depicted on the upper portion of the figure, as is the polynucleotide encoding the chimeric P2P2AQP1fAQP1f chimera. The *M. haemolytica* P2P2AQP1fAQP1fΔlktCAV4 cassette is depicted on the lower portion of the figure. The leukotoxin promotor is shown by a light grey arrow; the lktC-lktA intergenic region is shown by a white arrow; the polynucleotide encoding the added leukotoxin NE is shown by striped back dashes; the leukotoxin A gene portions present are shown by a dotted arrow; the polynucleotide encoding leukotoxin A GRR is shown by a diagonal brick pattern; the polynucleotide encoding the native leukotoxin NE is shown by alternating horizontal dashes; the polynucleotides encoding P2 are shown by horizontal bricks; and the polynucleotides encoding the AQP1 fragment are shown by diagonal stripes.

The polypeptide produced by the P2P2AQP1fAQP1fΔlktCAV4 cassette was separated from the cell culture, and stored at −80° C. until used.

Example 3

Cattle Vaccination and Challenge

Calves were vaccinated with the polypeptide produced by the P2P2AQP1fAQP1f-ΔlktCAV4 cassette mixed with Montanide ISA50V2.

Prior to vaccination, and 70 days, 105 days, and 135 days post vaccination blood was collected for serum production. The P2-P2-Aquapep-Aquapep-ΔlktCAV4 cassette was resuspended in PBS, and mixed with Montanide ISA50V2. An emulsion was prepared by mixing the cassette in PBS with Montanide ISA50V2 using two Leur-Lock-connected syringes. A syringe containing 2 ml of the emulsion was prepared for each calf. A first booster vaccination was administered after 4 weeks, and a second booster vaccination was administered 4 weeks later. A first tick infestation was performed 2 weeks after the second booster, and a second tick infestation was performed 4 weeks later.

Figure 3:
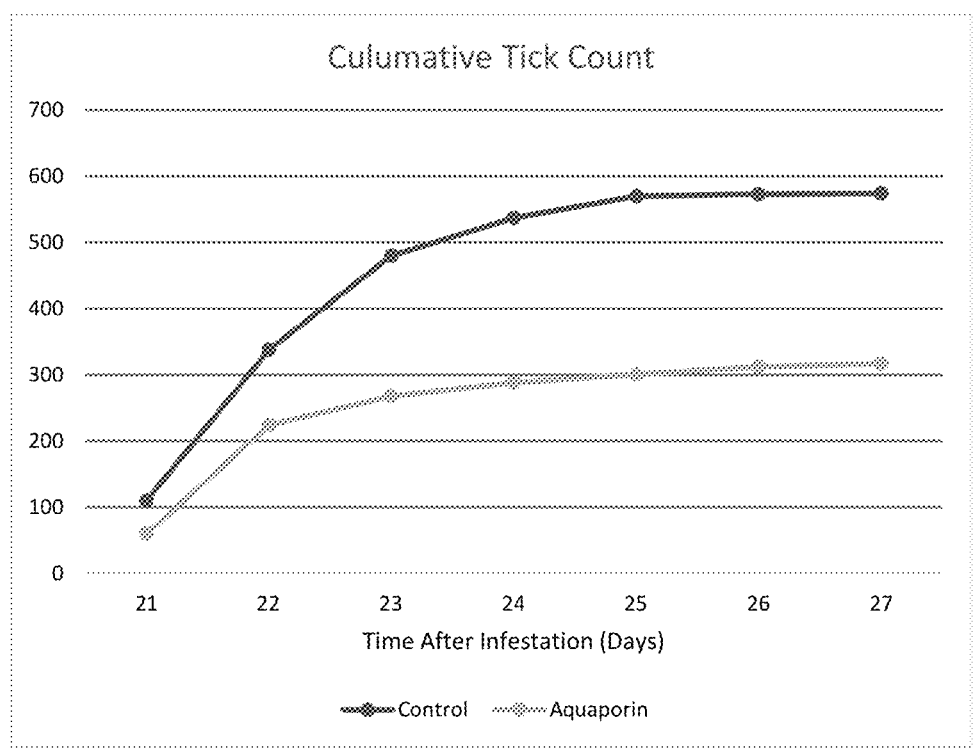
FIG. 3 depicts a graph of the cumulative tick count of control calves, or calves treated with the P2-P2-Aquapep-Aquapep-ΔlktCAV4 chimeric peptide. The X axis presents the time after tick infestation in days. The Y axis presents the mean number of ticks in all calves in each group.

Starting 21 days after infestation, the ticks were counted each day up to day 26. The cumulative tick count determined is shown in FIG. 3. In control calves, at day 21 there were approximately 100 ticks per calf, and this numbered increased with time, until it plateaued at days 25 and 26 with over 550 ticks per calf. In calves vaccinated with the P2-P2-Aquapep-Aquapep-ΔlktCAV4 chimeric peptide, at day 21 there were approximately 50 ticks per calf, and this number increased with time until it plateaued at days 25 and 26 with approximately 325 ticks per calf.

Thus, the antigen expressed by the P2P2AQP1fAQP1fΔlktCAV4 cassette presented a reduction in tick infestation with time as compared to control.

Example 4

Antibody Response

Antibody response to the AQP1 peptide and the leukotoxin epitope was positive for all vaccinated animals.

Indirect ELISA assays were conducted using immobilized biotinylated biosynthetic peptides commercially synthesized by Peptide 2.0 (Chantilly, Virginia, USA). N-terminal biotin and a hinge region were added to the polypeptide having the amino acid sequence set forth in SEQ ID NO 16 to produce the labeled AQP1 peptide: SGSGALVFATYKDAIEHFDQ-GIRQV TGEKATAGIFATYPRPHVSTLTCFIDQVIAT (set forth in SEQ ID NO: 20). N-terminal biotin and a hinge region were added to a peptide containing a leukotoxin neutralizing epitope to result in labeled Lkt peptide: SGSG-FREADFAKEVPNYKATKDEKIEEIIGQNGERI (set forth in SEQ ID NO: 21). The peptides were applied at 1 uM/well to streptavidin plates (Pierce Catalog #15120). Sera samples obtained from each calf at days 0, 70, 105, and 135 post inoculation were tested at 1:50 dilution in quadruplicate Alkaline phosphatase labelled rabbit anti-bovine IgG whole molecule were used as secondary antibody at 1:1000 dilution (Sigma catalog #A0705). PNP (Sigma catalog #N2770) was used as substrate. Results were reported as OD450(test date) minus OD450(day0).

Figure 4A:
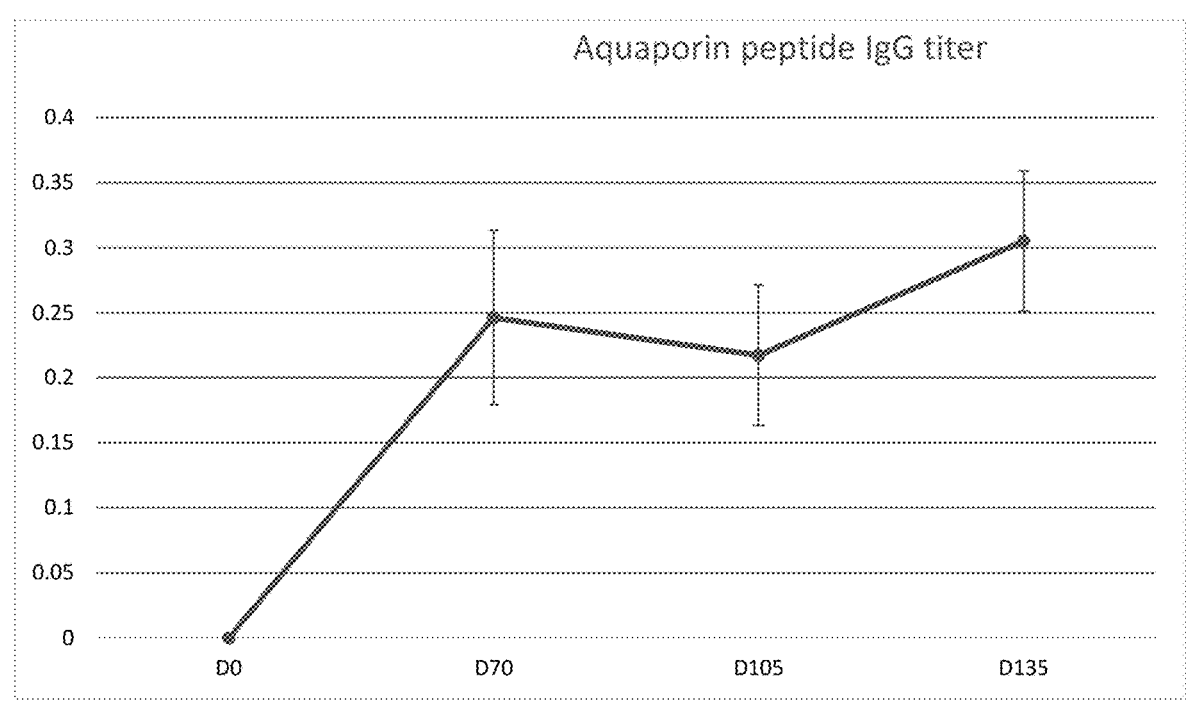
FIG. 4A and FIG. 4B depict graphs of the mean antibody titers against AQP1 peptide and LktA peptide determined using indirect ELISA.
Figure 4B:
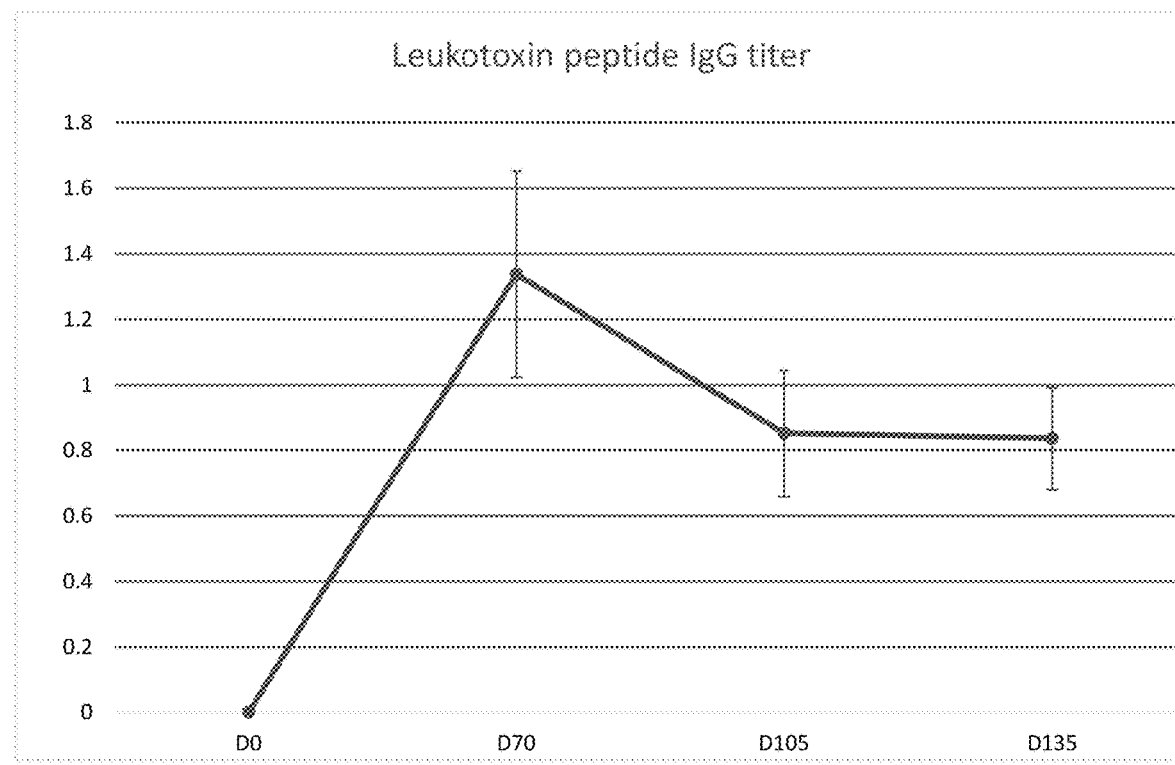

The results obtained with AQP1 peptide and anti-leukotoxin peptide are shown on FIG. 4A and FIG. 4B respectively. Mean antibody titers against both AQP1 peptide and LktA peptide exhibited increases between day 0 and day 70, then remained elevated through the remainder of the trial. Variation in individual animal responses were evident, as can be observed in the sizable error bars for each date (SEM).

Delivery of the vaccine resulted in demonstrable antibody responses against both antigens of interest in the vaccine. The measured antibodies correlated with protection against experimental infestation with *Rhipicephalus microplus*.

Example 5

Deer Vaccination

Deer were vaccinated with the polypeptide produced by the P2P2AQP1AQP1-lktCAV4 cassette and the lktCAV4 cassette to evaluate antibody response in a cervid host.

The P2-P2-Aquapep-Aquapep-lktCAV4 polypeptide produced by the P2P2AQP1AQP1-lktCAV4 cassette and polypeptide produced by the lktCAV4 cassette were suspended in PBS, and a water-in-oil-in-water emulsion was prepared with Montanide ISA 201VG adjuvant. The preparation was at a final concentration of 50 micrograms polypeptide per 1 ml.

A 2 ml volume was delivered subcutaneously to each deer, and booster vaccinations were administered at weeks 3, 5, and 8. Blood was collected for serum on the day of primary immunization (day 0), and on weeks 2, 3, 5, 7, 8, 10, and 13. Indirect ELISA assays provide antibody titers over time. This data will show that delivery of the vaccine results in demonstrable antibody responses against both antigens of interest in the vaccine, and that the measured antibodies correlate with protection against experimental infestation with *Rhipicephalus microplus*.

Example 6

Cattle Vaccination

Calves (*Bos taurus*) were vaccinated with the polypeptide produced by the P2P2AQP1AQP1-lktCAV4 cassette and with the polypeptide produced by the lktCAV4 cassette.

The P2-P2-Aquapep-Aquapep-lktCAV4 and -lktCAV4 polypeptides were suspended in PBS, and a water-in-oil-in-water emulsion was prepared with Montanide ISA 201VG adjuvant. The preparation was at a final concentration of 50 micrograms polypeptide per 1 ml.

A 2 ml volume was delivered subcutaneously to each calf, and booster vaccinations were administered at weeks 3 and 5. Blood was collected for serum on the day of primary immunization (day 0), and on weeks 2, 3, and 5 post-vaccination.

As of 1 Mar. 2021, this study is ongoing and is currently in week 7. Future events will include a final booster vaccination at week 8, and blood collection for serum on weeks 7, 8, 10, and 13. Indirect ELISA assays will be used to evaluate antibody titers over time, and A tick challenge with *Rhipicephalus microplus* will commence 2 weeks after the final booster vaccination.

The effectiveness of the vaccine will be tested as in Examples 3 and 4.

We claim:

1. A polypeptide comprising at least one copy of a tick *Rhipicephalus microplus* aquaporin 1 protein (AQP1) fragment having the amino acid sequence as set forth in SEQ ID NO: 16 and at least one copy of a tetanus toxin P2 epitope having the amino acid sequence as set forth in SEQ ID NO: 14.

2. The polypeptide of claim 1, wherein the polypeptide has two copies of the AQP1 protein fragment.

3. The polypeptide of claim 1, wherein the polypeptide has two copies of the P2 epitope.

4. A composition comprising the polypeptide of claim 1.

5. The composition of claim 4, wherein the composition is a host cell, a vaccine, or an immunogenic composition.

6. The composition of claim 5, wherein the composition is a host cell selected from an attenuated *Mannheimia haemolytica* strain A1 bacterium, and an attenuated *M. haemolytica* strain A6 bacterium.

7. A vaccine or immunogenic composition comprising the polypeptide of claim 1, and optionally an adjuvant.

8. A method of provoking an immune response in an animal, the method comprising administering to the animal at least one effective dose of a composition of claim 6.

9. The method of claim 8, wherein the animal is a mammal.

10. A kit comprising the polypeptide of claim 1.

11. A kit comprising the composition of claim 4.

* * * * *